United States Patent [19]
Goldman et al.

[11] Patent Number: 5,187,073
[45] Date of Patent: * Feb. 16, 1993

[54] PROCESS FOR TRANSFORMING GRAMINEAE AND THE PRODUCTS THEREOF

[75] Inventors: Stephen L. Goldman, Toledo; Anne C. F. Graves, Bowling Green, both of Ohio

[73] Assignee: The University of Toledo, Toledo, Ohio

[*] Notice: The portion of the term of this patent subsequent to Jan. 5, 2010 has been disclaimed.

[21] Appl. No.: 436,187

[22] Filed: Nov. 13, 1989

Related U.S. Application Data

[63] Continuation of Ser. No. 67,902, Jun. 29, 1987, abandoned, which is a continuation-in-part of Ser. No. 880,271, Jun. 30, 1986, abandoned.

[51] Int. Cl.$^5$ .................. C12N 15/00; C12R 1/41
[52] U.S. Cl. ..................... 435/172.3; 435/252.2; 435/320.1; 935/67
[58] Field of Search ............ 435/172.3, 320.1, 252.2; 935/29, 30, 35, 64, 67

[56] References Cited

PUBLICATIONS

Abbe & Stein, *Amer. J. Bot.*, 41, 285 (1954).
Abel, Nelson, De, Hoffman, Rogers, Fraley and Beachy, *Science*, 232, 738 (1986).
M. Bagdasarian, Lury, Ruckert, Franklin, M. M. Bagsasarian, Frey, Timmis, *Gene*, 16, 237 (1981).
Bevan, Barnes, and Chilton, *Nucleic Acid. Res.*, 11, 369 (1983).
Boocock and Coggins, *FEBS Letters*, 154, 127 (1983).
Brar, Rambold, Gamborg and Constabel, *Z. Planzenphysiol Bd.*, 95, S. 377 (1979).
Casse, Boucher, Julliot, Michel and Denaire, *J. Gen. Microbiology*, 113, 229, (1979).
Chilton, Saiki, Yadav, Gordon and Quetier, *Proc. Natl. Acad. Sci.*, 77, 4060 (1980).
Coe and Sarkar, *Crop Sci.*, 6, 432 (1966).
Comai, Facciotti, Giatt, Thompson, Rose and Stalker, *Nature*, 317, 741 (1985).
De Cleene and De Ley, *The Botanical Review*, 42, 389 (1976).
DeGreve, Dhaese, Seurinck, Lemmers, Montagu and Schell, *J. Mol. Appl. Genet.*, 1, 499 (1983).
Depicker, Stachel, Dhaese, Sambryski and Goodman, *J. Mol. Appl. Genet.*, 1, 561 (1983).

(List continued on next page.)

*Primary Examiner*—David T. Fox
*Attorney, Agent, or Firm*—Marshall & Melhorn

[57] ABSTRACT

A method of producing transformed Gramineae comprising making a wound in a seedling in an area of the seedling containing rapidly dividing cells and inoculating the wound with vir+ *Agrobacterium tumefaciens*. Also, this same method wherein the vir+ *A. tumefaciens* contains a vector comprising genetically-engineered T-DNA. There are further provided a transformed pollen grain of a Gramineae, a pollen grain of a Gramineae produced by a plant grown from a seedling infected with vir+ *A. tumefaciens*, a pollen grain of a Gramineae produced by a plant grown from a seedling infected with vir+*A. tumefaciens* containing a vector comprising genetically-engineered T-DNA, a pollen grain of a Gramineae whose cells contain a segment of T-DNA, and Gramineae derived from each of these pollen grains. There are also provided a transformed Gramineae plant, a transformed Gramineae plant derived from a seedling infected with vir+ *Agrobacterium tumefaciens*, a transformed Gramineae plant derived from a seedling infected with vir+ *A. tumefaciens* containing a vector comprising genetically-engineered T-DNA and a Gramineae plant whose cells contain a segment of T-DNA. Finally, there are provided transformed Gramineae derived from seedlings infected with vir+ *Agrobacterium tumefaciens* and transformed Gramineae derived from seedlings infected with vir+ *A. tumefaciens* containing a vector comprising genetically-engineered T-DNA.

4 Claims, 7 Drawing Sheets

OTHER PUBLICATIONS

Depicker, De Wilde, G. De Vos, R. De Vos, Montagu and Schell, *Plasmid*, 3, 193 (1980).

Ditta, Stanfield, Corbin and Helinski, *Proc. Natl. Acad. Sci.*, 77, 7347 (1980).

Duncan, Williams, Zehr and Widholm, Planta, 165, 322 (1985).

Fromm, Taylor and Walbot, *Nature*, 319, 791 (1986).

Graves, Ph.D. Dissertion, Bowling Green State University (1982).

Hain, Stabel, Czernilofskv. Steinbiss, Herrera-Estrella and Schell, *Molec. Gen. Genet.*, 199, 161 (1985).

Hernalsteens, Thia-Toong, Schell and Montagu, *The EMBO J* 3, 3039 (1984).

Hooykaas-Van Slogteren, Hooykaas and Schilperoort, *Nature*, 311, 763 (1984).

Kao, Perry and Kado, *Mol. Gen. Genet.*, 188, 425 (1982).

Krens, Molendijk, Wullems and Schilperoort, *Nature*, 296, 72 (1982).

Lin and Kado, *Can. J. Microbiol.*, 23, 1554 (1977).

Lippincott, Webb and Lippincott, *J. Bact.*, 90, 1955 (1965).

Lorz, Baker and Schell, *Mol. Gen. Genet.*, 199, 178 (1985).

Lundquist, Close and Kado, *Mol. Gen. Genet.*, 193, 1 (1984).

Marton, Wullems, Molendijk and Schilperoort, *Nature*, 277, 129 (1979).

Matthysse, *J. Bact.*, 154, 906 (1983).

Murashige and Skoog, *Physiol. Plant.*, 15, 473 (1962).

Nester, Gordon Amasino and Yanovsky, *Ann. Rev. Plant Physiol.*, 35, 387 (1984).

Otten, Vreugdenhil and Schilperoort, *Biochem. Biophys. Acta.*, 485, 263 (1977).

Otten and Schilperoort, *Biochem. Biophys. Acta.*, 527, 497 (1978).

Otten, DeGreve, Hernalsteens, Montagu, Schieder, Straub and Schell, *Molec. Gen. Genet.*, 183, 209 (1981).

Paszkowski, Shillito, Saul, Mandak, T. Hohn, B. Hohn and Potrykus, *The EMBO J.*, 3, 2717 (1984).

Potrykus, Harms and Lorz, *Theor. Appl. Genet.*, 54, 209 (1979).

Potrykus, Saul, Petruska, Paszkowski and Shillito, *Mol. Gen. Genet.*, 199, 183 (1985).

Rao, B. Lippincott and J. Lippincott, *Physiol. Plant.*, 56, 374 (1982).

Sass, in Corn and Corn Improvement 63-87 (G. F. Sprauge, ed., 1955).

Sciaky, Montoya and Chilton, *Plasmid*, 1, 238 (1978).

Schafer, Gory, Kahl, *Nature*, 327, 529 (1987).

Stalker, Hiatt & Comai, *The J. Biol. Chem.*, 260, 4724 (1985).

Stonier, *J. Bacteriol.*, 79, 889 (1959).

Thomashow, Nutter, Postle, Chilton, Blattner, Powell, Gordon and Nester, *Proc. Natl. Acad. Sci.*, 77, 6448 (1980).

Toole, *Amer. Jour. Bot.*, 11, 325 (1924).

Turgeon, Wood and Braun, *Proc. Natl. Acad. Sci.*, 73, 3562 (1976).

Waldron, Murphy, Roberts, Gustafson, Armour and Malcolm, *Plant Molecular Biology*, 5, 103 (1985).

J. T. Watson, J. Tooze & D. T. Kurtz, *Recombinant DNA* 164-175 (1983).

Yadav, Postle, Saiki, Thomashow and Chilton, *Nature*, 287, 458 (1980).

Ohta, *PNAS*, 83, 715-19 (1986).

Korohoda et al., *Z. Pflanzenphysiol. Bol.*, 94, 95-99 (1979).

Morgun et al., *Mol. Biol (Kiev)*, 18, 50-53 (1977).

Abdullah, Cocking and Thompson, *Bio/Technology*, 4, 1087 (1986).

An, Watson, Stachel, Gordon, and Nester, *The EMBO Journal*, 4: 277-284 (1985).

Buchanan-Wollaston, Passiatore and Cannon, *Nature*, 328, 172 (1987).

Byrne, McDonnell, Wright and Carnes, *Plant Cell, Tissue and Organ Culture*, 8, 3-15 (1987).

Bytebier, Deboeck, DeGreve, Van Montagu, and Hernalsteens, *Proc. Nat'l Acad. Sci USA*, 84, 5345-5349 (1987).

Chee, Klassy & Slightom, *Gene*, 41, 47-57 (1986).

Crossway, Oakes, Irvine, Ward, Knauf and Shewmaker, (1986) *Mol. Gen. Genet.*, 202, 179-185.

(List continued on next page.)

OTHER PUBLICATIONS

De Cleene, *Phytopath Z*, 113, 81–89 (1985).

Facciotti, O'Neal, Lee and Shewmaker, *Bio/Technology* 3, 241 (1985).

Feldmann, and Marks, *Mol. Gen. Genet*, 208, 1–9 (1987).

Fraley, Rogers, Horsch, Sanders, Flick, Adams, Bittner, Brand, Fink, Fry, Galluppi, Goldberg, Hoffmann and Woo, *Proc. Natl. Acad. Sci., USA*, 80: 4803–7 (1983).

Fromm, Taylor and Walbot, *Proc. Natl. Acad. Sci. U.S.A.*, 82, 5824–5828 (1985).

Graves and Goldman, Abstract, *Proceedings of the Crown Gall Conference*, p. 20 Sep. 1986.

Graves and Goldman, *Plant. Mol. Biol.*, 7, 43 (1986).

Grimsley, T. Hohn, Davies, and B. Hohn, *Nature*, 325, 177 (1987).

Grimsley, Ramos, Hein, and B. Hohn, *Bio/Technology*, 6, 185 (1988).

Kado and Liu, *Journal of Bacteriology*, 145, 1365 (1981).

Klein, Wolf, Wu and Sanford, *Nature*, 327, 70, (1987).

Kyozuka, Hayashi and Shimamoto, *Mol. Gen. Genet.*, 206, 408–413 (1987).

J. Lippincott, Margot and B. Lippincott, *J. Bact.*, 132, 824 (1977).

Murai et al., *Science*, 222, 476 (1983).

Owens and Cress, *Plant Physiol.*, 77, 87–94 (1985).

Slightom, Sun and Hall, *Proc. Nat'l Acad. Sci. USA*, 80, 1987 (1983).

Yamada, Zhi-Qi and Ding-Tai, *Plant Cell Reports*, 5, 85 (1986).

Graves and Goldman, *Journal of Bacteriology*, 169, 1745 (1987).

Korohoda and Strzalka, *Z. Planzenphysiol. Bd.*, 94, 95–99 (1979).

Morgun, Chernykh, Kordyum, *Chem. Abstracts*, 88(11), 71618k (1977) (*Mol. Biol.* (Kiev), 18, 50 (1977)).

Ohta, *Proc. Natl. Acad. Sci. USA*, 83, 715–19 (1986).

de la Pena, Lorz and Schell, *Nature*, 325, 274 (1987).

*Chemistry and Engineering News*, p. 21, Jul. 13, 1987.

*The Economist*, p. 92, Mar. 7, 1987.

PROCESS FOR TRANSFORMING GRAMINEAE AND THE PRODUCTS THEREOF

This is a continuation of application Ser. No. 07/067,902, filed Jun. 29, 1987, now abandoned, which was a continuation-in-part of application Ser. No. 06/880,271, filed Jun. 30, 1986, now abandoned.

BACKGROUND OF THE INVENTION

Virulent strains of the soil bacterium *Agrobacterium tumefaciens* are known to infect dicotyledonous plants and to elicit a neoplastic response in these plants. The tumor-inducing agent in the bacterium is a plasmid that functions by transferring some of its DNA into its host plant's cells where it is integrated into the chromosomes of the host plant's cells. This plasmid is called the Ti plasmid, and the virulence of the various strains of *A. tumefaciens* is determined in part by the vir region of the Ti plasmid which is responsible for mobilization and transfer of the T-DNA. The T-DNA section is delimited by two 23-base-pair repeats designated right border and left border, respectively. Any genetic information placed between these two border sequences may be mobilized and delivered to a susceptible host. Once incorporated into a chromosome, the T-DNA genes behave like normal dominant plant genes. They are stably maintained, expressed and sexually transmitted by transformed plants, and they are inherited in normal Mendelian fashion.

The lump of plant tumor tissue that grows in an undifferentiated way at the site of the *A. tumefaciens* infection is called a crown gall. Cells of crown gall tumors induced by *A. tumefaciens* synthesize unusual amino acids called opines. Different strains of *A. tumefaciens* direct the synthesis of different opines by the crown gall cells, and the particular opine induced is a characteristic of the strain which infected the plant. Further, the ability to catabolize the particular opine induced by a given strain is also characteristic of that strain.

Opines are not normally synthesized by *A. tumefaciens* or by the uninfected host plants. Although it is the T-DNA which codes for the enzymes involved in the synthesis of the opines, the opine synthases, these genes are expressed only in infected plant tissue. This type of expression is consistent with the observation that these genes are under the control of eukaryotic regulatory sequences on the T-DNA.

The most common opines are octopine and nopaline. The opine synthase that catalyzes the synthesis of octopine is lysopine dehydrogenase, and the opine synthase that catalyzes the synthesis of nopaline is nopaline dehydrogenase.

When crown gall cells are put into culture, they grow to form a callus culture even in media devoid of the plant hormones that must be added to induce normal plant cells to grow in culture. A callus culture is a disorganized mass of relatively undifferentiated plant cells. This ability of crown gall cells to grow in hormone-free media is also attributable to the presence of the T-DNA in the transformed host plant cells since genes which direct the synthesis of phyto-hormone are also associated with the T-DNA.

A DNA segment foreign to the *A. tumefaciens* and to the host plant which is inserted into the T-DNA by genetic manipulation will also be transferred to host plant's cells by *A. tumefaciens*. Thus, the Ti plasmid can be used as a vector for the genetic engineering of host plants. Although, in wild type *A. tumefaciens* there is only one Ti plasmid per bacterium, in genetically-engineered *A. tumefaciens*, the vir region and the T-DNA do not have to be carried on the same Ti plasmid for transfer of the T-DNA to occur. The vir region and the T-DNA can be carried on separate plasmids contained within the same Agrobacterium.

It has generally been assumed that the host range of *A. tumefaciens* was limited to the dicotyledons, and that transformation of monocotyledons could not be effected with this bacterium. Indeed, no one has reported the transformation of any member of the monocotyledonous Gramineae family by infection with *A. tumefaciens*.

However, recently, Hooykaas-Van Slogteren et al., in *Nature*, 311, 763 (1984), reported the production of small swellings at wound sites infected with *A. tumefaciens* on monocotyledons of the Liliaceae and Amaryllidaceae families. Opines were detected in plant cells taken from the wound sites of the infected plants.

Also, Hernalsteens et al. reported in *The EMBO Journal*, 3, 3039 (1984) that cultured stem fragments of the monocotyledon *Asparagus officinalis*, a member of the family Liliaceae, infected with *A. tumefaciens* strain C58 developed tumorous proliferations. One of these tumorous proliferations could be propagated on hormone-free medium, and opines were detected in the established callus culture derived from this tumorous proliferation.

In 1982, Anne C. F. Graves reported in her Ph.D. Dissertation entitled "Some Tumorigenic Activities of *Agrobacterium Tumefaciens* (Smith and Town) Conn." (Bowling Green State University) that irregular masses of tissue developed on gladiolus discs in response to inoculations with *A. tumefaciens* C58N and B6. These masses of tissue appeared to be the same as, and have cellular morphology similar to, those that develop on potato tuber discs. Gladiolus is a member of the monocotyledonous Iridaceae family. A compound that co-migrated with the octopine standard during electrophoresis was found in the proliferations on the gladiolus discs that were induced by strain B6, and one that migrated just behind the octopine standard occurred in those induced by C58N. Also, octopine dehydrogenase was found in extracts of the cellular proliferations induced by *A. tumefaciens* B6 but not in those induced by *A. tumefaciens* C58N.

Dr. Graves also described the response of certain other monocots to inoculation with *A. tumefaciens*. No cellular proliferation was observed on ginger root rhizome discs, and the results with tulip bulb discs were inconclusive. Cellular proliferations on discs of the rhizomes of cattail and skunk cabbage were limited to several layers of clear cells at the ends of vascular bundles in the early spring.

DeCleene and DeLey in *The Botanical Review*, 42, 389 (1976) reported the results of an extensive study of the plant host range of *A. tumefaciens*. Their article teaches that monocots of the orders Liliales and Arales are susceptible to infection with *A. tumefaciens* but that monocotyledons in general are unsusceptible to *A. tumefaciens* infection. In particular, their article reports that the Gramineae tested were not susceptible to infection with *A. tumefaciens*. Susceptibility to *A. tumefaciens* infection was determined by whether a swelling or tumor developed at the wound site.

Lorz et al. in *Mol. Gen. Genet.*, 199, 178 (1985), Fromm et al in *Nature*, 319, 791 (1986) and Portrykus et al. in *Mol. Gen. Genet*, 199, 183 (1985) have reported the transformation of Gramineae by direct gene transfer to protoplasts. Protoplasts are plant cells from which the cell wall has been removed by digestion with enzymes. Lorz et al. transformed protoplasts of *Triticum monococcum* using a DNA construct containing the nopaline synthase promotor and the polyadenylation regulatory signal of the octopine synthase gene. Fromm et al discloses that the electroporation-mediated transfer of plasmid pCaMVNEO (comprising the cauliflower mosaic virus 35 S promoter, the neomycin phosphotransferase II gene from the transposon Tn5 and the nopaline synthase 3' region) into maize protoplasts results in stably-transformed maize cells that are resistant to kanamycin.

To obtain transformed plants from the transformed cells generated using either the infection techniques of Hooykaas-Van Slogteren et al., Hernalsteens et al., Graves and DeCleene and DeLey or the direct gene transfer techniques of Lorz et al., Fromm et al. and Portrykus et al., the plants would have to be regenerated from protoplasts or single cell cultures. However, no one has yet been able to regenerate plants from protoplasts or single cell cultures of the Gramineae. Indeed, no means of producing transformed plants or other transformed differentiated organs or tissues of the Gramineae is currently known, and no method yet exists for transforming the Gramineae in a manner which allows for the expression of exogenous DNA in agriculturally important forms or parts of the Gramineae such as seeds, pollen, ears or plants.

Finally, PCT International Publication No. WO 86/00931 (Simpson et al.) published Feb. 13, 1986, teaches in vivo methods for transforming and regenerating intact plants. This patent application discloses that the methods of the invention can be used for the transformation of any plant that forms a shooty tumor following infection with an *A. tumefaciens* shooty mutant strain. However, as noted above, the Gramineae are not known to produce tumors or even swellings in response to inoculation with *A. tumefaciens*. In the practice of the present invention, no tumors, swellings or cellular proliferations of any kind have been observed on the Gramineae in response to inoculation with *A. tumefaciens*.

SUMMARY OF THE INVENTION

According to the present invention, there is now provided a method of producing transformed Gramineae comprising making a wound in a seedling in an area of the seedling containing rapidly dividing cells and inoculating the wound with vir+ *A. tumefaciens*. In the preferred practice of the invention, the wound is made in an area of the seedling which gives rise to the germ line cells. Also, preferred is the use of vir+ *A. tumefaciens* which contains a vector comprising genetically-engineered T-DNA.

According to another aspect of the invention, there are provided: (1) transformed pollen grains; (2) a transformed pollen grain produced by a plant grown from a seedling infected with vir+ *A. tumefaciens;* (3) a transformed pollen grain produced by a plant grown from a seedling infected with vir+ *A. tumefaciens* which contains a vector comprising genetically-engineered T-DNA; (4) a pollen grain whose cells contain at least a segment of T-DNA; and (5) Gramineae derived from each of these four pollen grains. In addition, there are provided: (1) a transformed Gramineae plant; (2) a transformed Gramineae plant derived from a seedling infected with vir+ *A. tumefaciens;* (3) a transformed Gramineae plant derived from a seedling infected with vir+ *A. tumefaciens* which contains a vector comprising genetically-engineered T-DNA; and (4) a Gramineae plant whose cells contain a segment of T-DNA. Finally, there are provided transformed Gramineae derived from seedlings infected with vir+ *A. tumefaciens* and transformed Gramineae derived from seedlings infected with vir+ *A. tumefaciens* which contains a vector comprising genetically-engineered T-DNA.

The invention is clearly useful since it provides, for the first time, a method for transforming Gramineae which results in the production of transformed differentiated organs and tissue such as leaves, plants and pollen. Thus, the invention provides, for the first time, a method of transforming Gramineae which allows for the expression of exogenous DNA in agriculturally important forms or parts of the Gramineae. Many of the Gramineae (such as corn, oats, rye, barley, sorghum, rice and wheat) are, of course, commercially important food sources for humans and other animals, and the invention allows for the development of strains of Gramineae having altered or superior traits, such as higher yielding strains and strains having resistance to herbicides or better nutritional value, by providing a means whereby exogenous DNA coding for such traits can be incorporated into the Gramineae.

BRIEF DESCRIPTION OF THE DRAWINGS

FIGS. 1–18 show a corn seedling which is ninety-six hours old.

FIG. 6 is a drawing of a developed electrophoretogram which is the result of the electrophoresis of the products produced by incubating the cell-free extracts of single seedlings of yellow Iochief corn inoculated with *A. tumefaciens* strain CA19 with lysopine dehydrogenase reaction medium.

FIG. 7 is a drawing of a developed electrophoretogram which shows the results of the electrophoresis of the products produced by incubating the cell-free extracts of single C58-inoculated seedlings of strain PA91 corn with nopaline dehydrogenase reaction medium.

FIG. 8 is a restriction site and function map of plasmid pCEL30.

FIG. 9 is a restriction site and function map of plasmid pCEL44.

FIG. 10 is a drawing of developed paper electrophoretogram which shows the results of the electrophoresis of the products produced by incubating cell-free extracts of single B6-inoculated rye seedlings with lysopine dehydrogenase reaction medium.

FIG. 11 is a drawing of a developed paper electrophoretogram which shows the results of the electrophoresis of the products produced by incubating cell-free extracts of single B6-inoculated barley seedlings with lysopine dehydrogenase reaction medium.

FIG. 12 is a drawing of a developed paper electrophoretogram showing the results of the electrophoresis of the products produced by incubating cell-free extracts of single C58-inoculated oat seedlings with nopaline dehydrogenase reaction medium.

FIG. 13 is a drawing of a developed electrophoretogram which is the result of the electrophoresis of the products produced by incubating the cell-free extracts of single C58-inoculated wheat seedlings with nopaline dehydrogenase reaction medium and with lysopine dehydrogenase reaction medium.

FIG. 14 is a drawing of a developed electrophoretogram showing assays for enzymatic activity in the upper leaves of transformed plants.

Figure 1A:
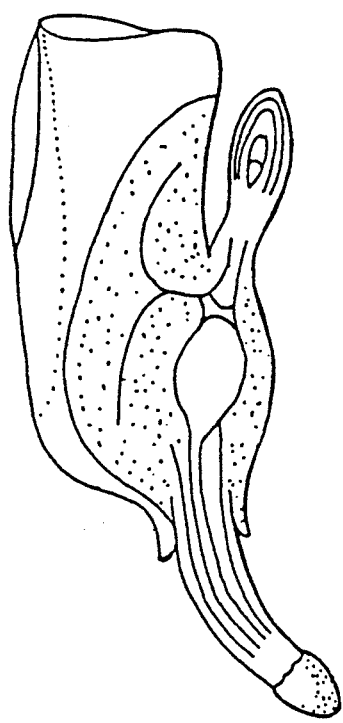
FIG. 1A is the side view of the seedling.

In all of the drawings where they are used, the designations "O" and "OCT" mean octopine, and the designations "N" or "NOP" mean nopaline. These designations are used on the drawings to refer to the lane of the electrophoretogram containing the synthetic octopine or nopaline standard or to show the location of spot formed by the synthetic octopine or nopaline standard after electrophoresis.

In some of the drawings there are spots which do not co-migrate with either the synthetic octopine or nopaline standards. These spots are formed by unreacted reactants in reaction media or are formed by naturally-occurring materials found in the cell-free extracts of the corn seedlings.

DETAILED DESCRIPTION OF THE PRESENTLY PREFERRED EMBODIMENTS

According to the invention, there is provided a method of producing transformed Gramineae comprising making a wound in a seedling in an area of the seedling containing rapidly dividing cells and inoculating the wound with vir+ *A. tumefaciens*. The term Gramineae, as used herein, is meant to include all of the forms and parts of the Gramineae, including plants, seeds, seedlings, pollen, kernels, ears, leaves, stalks and embryos. Similarly, the terms "corn", "oats", "wheat," "rye" and "barley" are meant to include all forms and parts of the corn, oats, wheat, rye or barley. "Transformed" is used herein to mean genetically modified by the incorporation of exogenous DNA into cells. "Exogenous DNA" is DNA not normally found in the strain of Gramineae which is to be transformed. Exogenous DNA may be obtained from prokaryotic or eukaryotic sources, including strains of Gramineae other than the one to be transformed.

In practicing the method of the invention, the strain of Gramineae to be transformed is sterilized and is then germinated until the radicle (primary root) and stem emerge from the seed. This occurs after about four days of germination, but this time may be shortened by first soaking the seeds.

The wound is preferably made in an area of rapidly dividing cells which gives rise to germ line cells. After making the wound, the seedling is inoculated by dripping a solution of vir+ *A. tumefaciens* into the wound. Vir+ *A. tumefaciens* are bacteria which are capable of mobilizing and transferring T-DNA into host plant cells, and an *A. tumefaciens* carrying a plasmid, whether natural or engineered, coding for these functions is vir+. Thus, a strain of *A. tumefaciens* that carries a wild-type Ti plasmid is vir+ and can be used in the present invention. Many such strains are known and are publicly available. See e.g., American Type Culture Collection Catalogue (ATCC) of Strain I, p. 66 (15th edition, 1982). The vir+ region of a wild type Ti plasmid can be used to mobilize and transfer T-DNA on the same Ti plasmid or to deliver T-DNA on another plasmid contained in the same bacterium. In addition, the mobilization and transfer functions can be supplied by helper plasmids. Such helper plasmids have been described by Ditta et al. in PNAS, 77, 7347 (1980) and by Bagdasarian et al. in *Gene*, 16, 237 (1981). Thus, a strain of *A. tumefaciens* that carries a helper plasmid is also vir+. Finally, the mobilization and transfer functions may be coded on the same engineered plasmid which contains the T-DNA, and bacteria containing such a plasmid are also vir+.

The T-DNA transferred by the vir+ *A. tumefaciens* may be native T-DNA or may preferably be genetically-engineered T-DNA. Genetically-engineered T-DNA is a DNA construct comprising T-DNA border sequences, a heterologous gene and a transcription unit connected in operable order. Methods of preparing such constructs are known in the art.

A heterologous gene is a gene which is not normally found in the T-DNA and which is also not normally found in the DNA of the strain of Gramineae which is to be transformed. Heterologous genes may be isolated from prokaryotic and eukaryotic sources, including strains of Gramineae other than the one to be transformed. Of particular interest are those heterologous genes which confer agronomically significant traits on plants containing them.

The heterologous gene is flanked by a transcription unit containing, e.g., promotors and terminators, which allow for expression of the heterologous gene in the strain of Gramineae to be transformed. The heterologous gene-transcription-unit construct is flanked by the border sequences. Any T-DNA border sequence, native or synthesized, can be used to flank the heterologous-gene-transcription-unit construct as long as the border sequence functions to integrate the heterologous gene into the cell genome of the strain of Gramineae to be transformed. The genetically-engineered T-DNA is linked to a DNA fragment containing a replicon that is functional in Agrobacterium to form a vector.

After the seedlings are inoculated with the vir+ *A. tumefaciens*, they are incubated until transformation has taken place at which time the seedlings are planted and allowed to grow at least until such time as they have produced pollen. It is interesting to note that using the method of the invention, no tumorous growth of any kind, including crown galls, calli or tumorous overgrowths, has been observed, even on the original inoculated seedling.

By inoculating the seedlings in the preferred area, transformation of pollen has been achieved. The resulting transformed pollen can be used to fertilize transformed and untransformed plants. The embryos can be excised from the resultant progeny ears and grown to produce transformed plants. Alternatively, of course, the plants resulting from this mating can be allowed to produce seeds which are, in turn, used to grow transformed whole plants which produce another crop of seeds. Thus, future-generations can be derived from the original transformed seedling by sexual reproduction. Those skilled in the art will recognize that various and numerous progeny carrying the trait coded for by the exogenous DNA can be produced using known breeding techniques.

TRANSFORMATION OF CORN

EXAMPLE I

A. Preparation of Bacteria

A single colony of the *A. tumefaciens* strain B6 was inoculated into a yeast extract broth (YEB) containing 0.1% yeast extract, 0.8% nutrient broth and 0.5% sucrose dissolved in water. The yeast extract and nutrient broth were purchased from Difco Laboratories, Detroit, Mich. The sucrose was purchased from either Fisher Scientific, Detroit, Mich., or Sigma, St. Louis, Mo. The bacteria were incubated in the YEB for 48 hours at 27° C. in a shaking water bath or until such time as they had reached a final concentration of $3.8 \times 10^9$ cells per milliliter.

The B6 strain is a standard wild type strain of *A. tumefaciens*. It is virulent (vir+), and it codes for the production of lysopine dehydrogenase in suitable plant hosts. It was obtained from James and Barbara Lippincott, Northwestern University, Evanston, Ill. Some of its properties have been described in Stonier, *J. Bact.*, 79, 889 (1960). The B6 strain is also on deposit at the American Type Culture Collection (ATCC), Rockville, Md., and it has been given accession number 23308.

B. Preparation of Corn

Seeds of the inbred yellow Iochief strain of corn were obtained from The Andersons, Maumee, Ohio, or from Botzum, 43 East Market, Akron, Ohio. This strain is a standard strain which is available commercially.

The yellow Iochief seeds were sterilized using the following procedure. The seeds were first immersed for two minutes in a solution containing 7 parts 95% ethanol and 2.5 parts distilled water. Next, the seeds were incubated for five minutes in a solution of 0.5% (weight/volume) $HgCl_2$ in distilled water. Next, the seeds were washed for a total of thirty minutes in a solution of 15% (volume/volume) Clorox (Clorox is an aqueous solution containing 5.25% sodium hypochlorite) and 0.1% (volume/volume) of a liquid dishwashing detergent such as Palmolive or another suitable wetting agent in distilled water. Finally, the seeds were washed five times in sterile double distilled water.

The sterilized seeds were placed embryo side up on sterile moistened Whatman No. 3 filter paper contained in a sterile Petri dish. The seeds were incubated in the covered Petri dishes in constant darkness at 25° C. for four days. The filter paper was kept moist throughout the incubation period.

C. Inoculation of Seedlings with *A. tumefaciens*

Figure 1B:
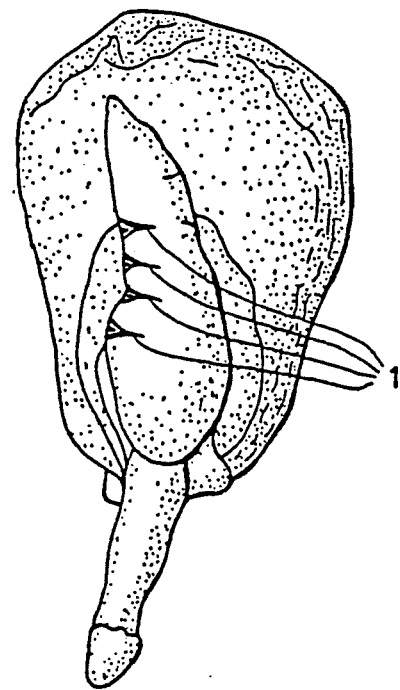
FIG. 1B is the front view of the same seedling.

The two primary areas of rapidly dividing cells in the corn seedling are the root cap and the area extending from the base of the scutellar node through the mesocotyl slightly beyond the coleoptile node, the locations of which are depicted in FIGS. 1A and 1B. The mesocotyl is the area between the scutellar node and the coleoptile node.

In the preferred practice of the invention, the wound is made in the area extending from the base of the scutellar node through and slightly beyond the coleoptile node because, included within the region, are tissues which give rise to germ line cells. In particular, found in this region is tissue which gives rise to the axillary primordia which, in turn, gives rise to tillers and to the ears (female reproductive organs). Also, located in this region is the apical meristem which gives rise to the tassle which, in turn, gives rise to the pollen (the male reproductive organs). By inoculating the seedling in this preferred area, transformation of germ line cells has been obtained.

Accordingly, a total of four wounds were made on the surface of each of the germinating corn seedlings prepared in part C of this example in an area which extends from the base of the scutellar node through and slightly beyond the coleoptile node. The wounds were made by visualizing a line which bisects this area longitudinally (the midline) as the seedling is viewed from the front as in FIG. 1B. The cuts were made perpendicular to the midline, from the midline to the outside edge of the seedling and from the front surface of the seedling, when the seedling is viewed as in FIG. 1B, through all of the tissue in the area where the cut is made. Thus, when a cut is made in the area of the scutellar node, the cut is made from the front surface through all of the tissue into the scutellum, and, when a cut is made in the mesocotyl, the cut is made from the front surface completely through all of the mesocotyl tissue. The four wounds are indicated by the numeral 1 in FIG. IB.

The wounds were inoculated by dripping a total of 100 ul of a $10^9$ cells/milliliter suspension of *A. tumefaciens* strain B6 in YEB, cultured as described above in part A, onto the four wounds. As a control, some seedlings were inoculated with 0.9% NaCl (saline). After receiving the inoculum, the seedlings were placed embryo side up on a layer of Bactoagar contained in a Petri dish, at 5 seedlings per dish. The Petri dish contained 20 milliliters of sterile Bactoagar (purchased from Difco Laboratories) at a concentration of 20 grams/liter in distilled water. The covered Petri dishes were incubated at 27° C. in constant darkness for an additional 7–14 days.

D. Assays

1. Assay For Enzyme Activity in Seedlings: At the end of the 7–14 day incubation period, the seedlings were homogenized in a 0.1M Tris-HCl buffer, 8.0, containing 0.5M sucrose, 0.1% (weight/volume) ascorbic acid and 0.1% (weight/volume) cysteine-HCl, using a Wheaton tissue grinder, until the homogenate had a homogeneous consistency. Since the seedlings were grown in the dark, pigment formation was retarded, and cell walls remained unusually soft. Thus, the cells of the seedlings broke open easily. Next, the homogenates were spun in a Fisher Microfuge at 13,000 xg for two minutes to obtain cell-free extracts.

A portion of the cell-free extract was added to an equal volume of a reaction medium designed to detect lysopine dehydrogenase activity. This reaction medium consisted of 30 mM L-arginine, 75 mM pyruvate and 20 mM NADH dissolved in 0.2M sodium phosphate buffer, pH 7.0. The enzyme reaction was allowed to proceed at room temperature for the times indicated below.

The products of the enzyme reaction were separated electrophoretically on Whatman 3MM paper. At the start of the enzyme reaction period (time zero), a 5 ul sample of the reaction mixture was spotted at the anodal site on the paper and dried. After 15 hours of reaction, another 5 ul sample of the reaction mixture was spotted on the paper and dried. Finally, a 5 ul sample of a 100 ug/ml solution of synthetic octopine purchased from Calbiochem, Division of American Hoescht, La Jolla, Calif., and a 5 ul sample of 100 ug/ml solution of synthetic nopaline purchased from Sigma, St. Louis, Mo., were spotted on the paper and dried.

Electrophoresis was performed in a formic acid (90.8%)/glacial acetic acid/water (5:15:80, volume/volume) solution, pH 1.8, for 2.5 hours at 450 volts. The paper was dried and then stained by dipping it into a solution containing one part 0.02% (weight/volume) phenanthrenequinone in absolute ethanol plus one part 10% (weight/volume) NaOH in 60% (volume/volume) ethanol. After drying, the spots were visualized under a long-wave ultraviolet lamp (366 nm).

Figure 2A:
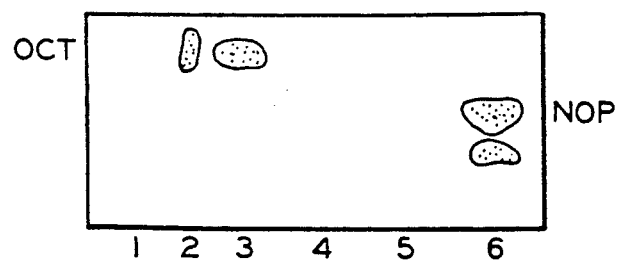
FIG. 2A is a drawing of developed paper electrophoretogram which shows the results of the electrophoresis of the products produced by incubating cell-free extracts of yellow Iochief corn seedlings inoculated with *A. tumefaciens* strain B6 with a reaction medium containing reagents which allow for the detection of lysopine dehydrogenase enzyme activity (lysopine dehydrogenase reaction medium). Certain controls were also electrophoresed.

The results of the electrophoresis of the products produced by adding the cell-free extracts of B6-inoculated seedlings to lysopine dehydrogenase reaction medium are shown in FIG. 2A. In that figure, lane 1 contains a sample of the reaction mixture produced by adding a portion of the cell-free extract of ten B6-inoculated seedlings to an equal volume of the lysopine dehydrogenase reaction medium at time zero, lane 2 contains the product produced by incubating a portion of the cell-free extract of ten B6-inoculated seedlings with an equal volume of lysopine dehydrogenase reaction medium for fifteen hours, lane 3 contains the synthetic octopine, lane 4 contains the product produced by adding a portion of the cell-free extract of ten saline-inoculated seedlings to an equal volume of lysopine dehydrogenase reaction medium at time zero, lane 5 contains the product produced by incubating a portion of the cell-free extract of ten saline-inoculated seedlings with an equal volume of lysopine dehydrogenase reaction medium for fifteen hours, and lane 6 contains the synthetic nopaline.

The results shown in FIG. 2A demonstrate that octopine production is caused by cell-free extracts of B6-inoculated corn seedlings, lane 2, but that no such production occurs in the saline control, lane 5. Furthermore, the amount of octopine produced, as measured by an increase in phenanthrenequinone fluorescence, increases in proportion to the time of incubation. While no octopine can be detected at time zero, lane 1, it is clearly present after fifteen hours of incubation, lane 2. Such results are in accord with the proposition that the reaction is enzyme catalyzed and that the enzyme extracted from the B6-infected corn seedlings is lysopine dehydrogenase. Since only transformed plant tissues are known to express the opine synthase genes, these results are also in accord with the proposition that the corn seedlings have been transformed by infection with the vir+ *A. tumefaciens* strain B6.

Figure 2B:
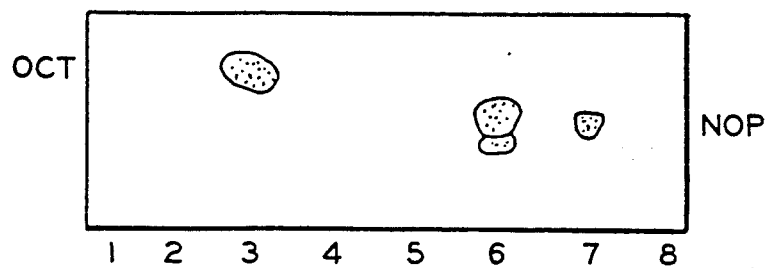
FIG. 2B is a drawing of a developed paper electrophoretogram which shows the results of the electrophoresis of the products produced by incubating cell-free extracts of yellow Iochief corn seedlings with a reaction medium containing reagents which allow for the detection of nopaline dehydrogenase enzyme activity (nopaline dehydrogenase reaction medium). Certain controls were also electrophoresed.

2. Assay For Substrate Specificity: Lysopine dehydrogenase catalyzes the synthesis of octopine but not of nopaline. In FIG. 2B the results of the electrophoresis of the products produced by adding extracts of seedlings to a reaction medium containing reagents which allow for the detection of nopaline dehydrogenase enzyme activity are presented. The nopaline dehydrogenase reaction medium consists of 60 mM L-arginine, 60 mM α-ketoglutarate and 16 mM NADH dissolved in 0.2M sodium phosphate buffer, pH 7.0. The α-ketoglutarate can be used as a substrate only by nopaline dehydrogenase. Lanes 1-6 in FIG. 2B are the same as lanes 1-6 of FIG. 2A except that the reaction medium is the nopaline dehydrogenase reaction medium. Thus, FIG. 2B shows that cell-free extracts of seedlings inoculated with strain B6 cannot use α-ketoglutarate in the condensation reaction with arginine to produce nopaline. This substrate specificity confirms the identity of the enzyme produced by seedlings transformed by strain B6 as lysopine dehydrogenase.

Figure 3A:
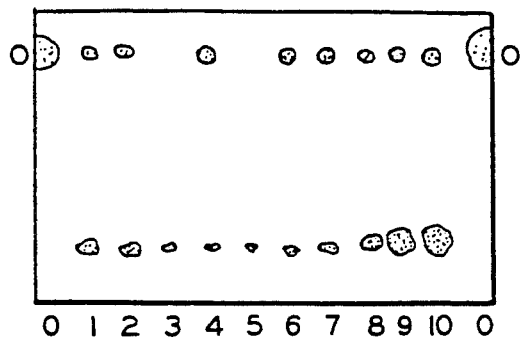
FIG. 3A is a drawing of a developed paper electrophoretogram which shows the results of the electrophoresis of the products produced by incubating cell-free extracts of single B6-inoculated yellow Iochief corn seedlings with lysopine dehydrogenase reaction medium.

3. Transformation Efficiency: To address this issue, assays of single seedlings were performed, and the number of cell-free extracts of single seedlings which produced octopine were determined. The results are shown in FIG. 3A where all ten lanes contain the product produced by incubating the cell-free extracts from single B6-inoculated seedlings with lysopine dehydrogenase reaction medium for four hours. As shown in FIG. 3A, eight of the ten lanes have a spot which stains with phenanthrenequinone and co-migrates with the octopine standard. Thus, the transformation frequency for this experiment was 80%.

Figure 4A:
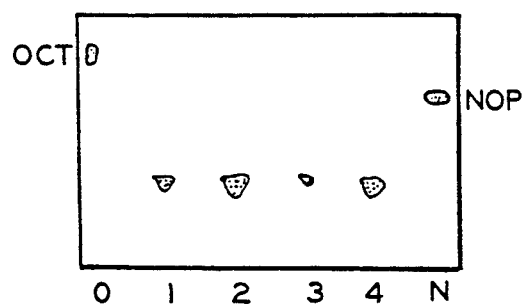
FIG. 4A is a drawing of a developed paper electrophoretogram which is the result of the electrophoresis of the cell-free sonicates of *A. tumefaciens* strains B6 and C58.
Figure 4B:
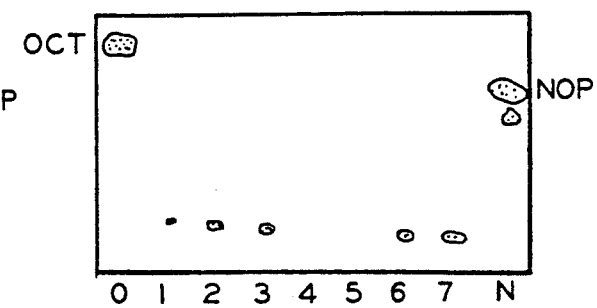
FIG. 4B is a drawing of a developed paper electrophoretogram showing the results of the electrophoresis of the products produced by incubating the cell-free sonicates of *A. tumefaciens* strains B6 and C58 for four hours with an appropriate reaction medium. Also electrophoresed were the reaction media alone.
Figure 4C:
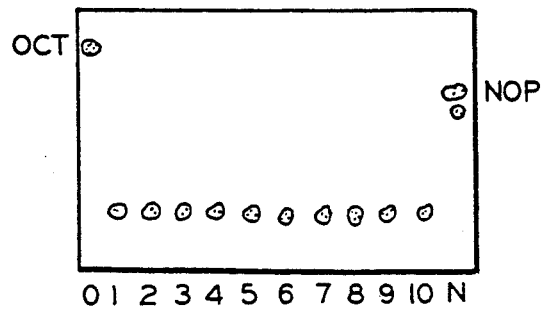
FIG. 4C is a drawing of a developed paper electrophoretogram which shows the results of the electrophoresis of the product produced by incubating the cell-free extracts of single uninfected seedlings of the yellow Iochief strain of corn for four hours with lysopine dehydrogenase reaction medium or with nopaline dehydrogenase reaction medium.

4. Controls: To rule out the possibility that the octopine produced was a consequence of some secondary and uninteresting event, several additional controls were done. As shown in FIG. 4A, electrophoresis of cell-free sonicates of a suspension of B6 cultured for 48 hours, as described above in part A, failed to disclose any stored octopine (lanes 1 and 2). Furthermore, when these sonicates were mixed with lysopine dehydrogenase reaction medium and incubated for four hours, no lysopine dehydrogenase activity could be detected. See FIG. 4B, lanes 1, 2 and 3 where the products of this incubation were electrophoresed. Thus, lysopine dehydrogenase activity is not found in bacterial cultures 48 hours old. Also, lysopine dehydrogenase reaction medium alone did not contain any octopine. See FIG. 4B, lane 4, where this reaction medium alone was electrophoresed. Similarly, no evidence is found for the existence of this dehydrogenase in uninfected corn seedlings. See FIG. 4C which shows an electrophoretogram in which lanes 1-5 contain the product produced by incubating cell-free extracts of uninfected single seedlings for four hours with lysopine dehydrogenase reaction medium. These results confirm that the presence of lysopine dehydrogenase activity in the cell-free extracts of B6-inoculated seedlings is due to the transformation of the seedlings and not to some secondary or uninteresting event.

EXAMPLE II

A. Preparation of Bacteria

A single colony of the *A. tumefaciens* strain C58 was inoculated into YEB, and the bacteria were incubated as described above in Example I, part A, for strain B6. The C58 strain is a standard wild type strain of *A. tumefaciens*. It is vir+, and it codes for the production of nopaline dehydrogenase in suitable plant hosts. It was obtained from James and Barbara Lippincott, Northwestern University, Evanston, Ill., or from Clarence Kado, University of California, Department of Plant Pathology, Davis, Calif. It has been described in Depicker et al, *Plasmid*, 3, 193 (1980) and Kao, et al, *Molec. Gen. Genet.*, 188, 425 (1982). Strain C58 is also on deposit at the ATCC and has been given accession number 33970.

B. Transformation of Corn

Seeds of the inbred yellow Iochief strain of corn were sterilized, germinated, inoculated and further incubated for 7-14 days as described above in Example I, parts B and C, except that the corn seedlings were inoculated with strain C58 rather than strain B6.

C. Assays

1. Assay For Enzyme Activity in Seedlings: At the end of the 7-14 day incubation period, cell-free extracts of the seedlings were prepared and were assayed for enzymatic activity as described above in Example I, part D, except that the reaction medium used was the one designed to assay for nopaline dehydrogenase activity. As set forth above in Example I, part D, this reaction medium consisted of 60 mM L-arginine, 60 mM α-ketoglutaric acid and 16 mM NADH dissolved in 0.2M sodium phosphate buffer, pH 7.0.

The results are shown in FIG. 2B. Lane 8 in FIG. 2B contains the product produced by mixing a portion of the cell-free extract of ten C58-inoculated seedlings with an equal volume of nopaline dehydrogenase reaction medium at time zero, and lane 7 contains the product produced by incubating a portion of the cell-free extract of ten C58-inoculated seedlings with an equal volume of nopaline dehydrogenase reaction medium for fifteen hours. Thus, FIG. 2B shows that nopaline is produced by the cell-free extracts of the C58-inoculated corn seedlings, lane 7, but that no such production was produced by the saline control, lane 5. Once again, the amount of nopaline produced, as measured by an increase in phenanthrenequinone fluorescence, increases in proportion to the time of incubation. While no nopaline can be detected in a reaction mixture at time zero, lane 8, it is clearly present after fifteen hours of incubation, lane 7, and such results are in accord with the proposition that the reaction is enzyme-catalyzed and that the enzyme extracted from C58-infected seedlings is nopaline dehydrogenase. Since only transformed plant tissues are known to express the opine synthase genes, these results are also in accord with the proposition that the corn seedlings have been transformed by infection with the vir+ *A. tumefaciens* strain C58.

2. Pyronopaline Assay: The synthesis of nopaline by extracts from seedlings transformed with C58 has been confirmed by criteria other than electrophoretic mobility. When nopaline is eluted from a paper chromatogram with water, evaporated by the application of a vacuum to reduce the volume and reacted with an equal volume of hot (100° C.) 2M acetic acid for one hour, pyronopaline is formed. The conversion reaction is diagnostic for nopaline and no other opine.

Figure 2C:
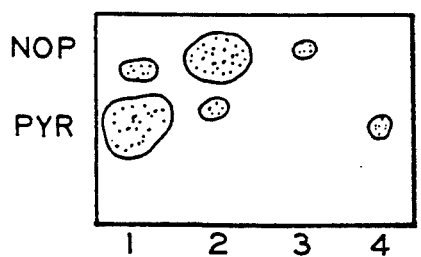
FIG. 2C is a drawing of a developed paper electrophoretogram which shows the presence or absence of pyronopaline in various materials.

In FIG. 2C, lane 1 is pyronopaline produced from synthetic nopaline by treating the synthetic nopaline with hot 2M acetic acid as described above, lane 2 is synthetic nopaline (some of which converts spontaneously to pyronopaline), lane 3 is the product produced by incubating a portion of the cell-free extract from ten C58-inoculated seedlings with an equal volume of the nopaline dehydrogenase reaction medium for fifteen hours, and lane 4 is this product treated with hot 2M acetic acid as described above. As can be seen, the product produced by incubating the cell-free extract from C58-inoculated seedlings with the nopaline dehydrogenase reaction mixture, lane 3, is totally converted to pyronopaline, lane 4, confirming that C58-inoculated seedlings produce nopaline dehydrogenase.

3. Catabolism of Nopaline: Finally, if nopaline is incubated with C58 and serves as its sole energy source, the bacteria will grow as this compound is degraded. However, B6 grown on a medium containing nopaline as the sole energy source will not break down the nopaline and will not divide since B6 lacks the specific opine oxidase which is necessary for the catabolism of nopaline.

Figure 2D:
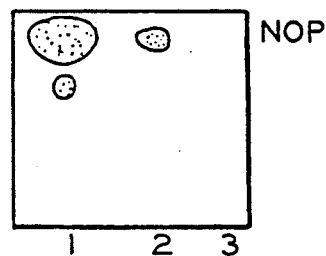
FIG. 2D is a drawing of a developed paper electrophoretogram. The materials electrophoresed were produced by the catabolism by certain strains of *A. tumefaciens* of the products produced by incubating cell-free extracts of yellow Iochief corn seedlings inoculated with *A. tumefaciens* strain C58 with nopaline dehydrogenase reaction medium. Certain controls were also electrophoresed.

An assay based on this principle was used to confirm the nopaline identity of the product produced by the cell-free extracts of C58-inoculated seedlings. The results of this assay are shown in FIG. 2D where lane 1 contains synthetic nopaline, lane 2 contains the product produced by incubating a portion of the cell-free extract of ten C58-inoculated seedlings with an equal volume of the nopaline dehydrogenase reaction medium for fifteen hours which has been electrophoresed, eluted with water and evaporated, as described above, in connection with the pyronopaline assay, and incubated with strain B6 for twenty-four hours, and lane 3 contains the product produced by incubating a portion of the cell-free extract of ten C58-inoculated seedlings with an equal volume of nopaline dehydrogenase reaction medium for fifteen hours which has been electrophoresed, eluted, evaporated and incubated with strain C58 for twenty-four hours. The product produced by the cell-free extracts of the C58-inoculated seedlings was consumed by strain C58, lane 3, but was not consumed by strain B6, lane 2, confirming that the product is nopaline.

Figure 3B:
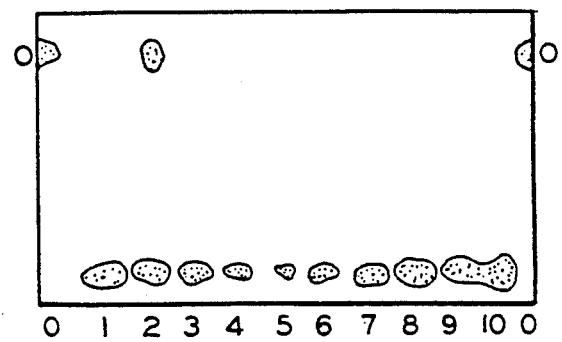
FIG. 3B is a drawing of a developed paper electrophoretogram which shows the results of the electrophoresis of the products produced by incubating cell-free extracts of single yellow Iochief corn seedlings inoculated with either *A. tumefaciens* strain A348 or strain 238MX with lysopine dehydrogenase reaction medium.
Figure 3C:
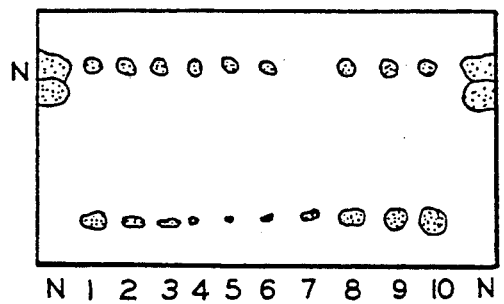
FIG. 3C is a drawing of a developed paper electrophoretogram showing the results of the electrophoresis of the products produced by incubating cell-free extracts of single C58-inoculated yellow Iochief corn seedlings with nopaline dehydrogenase reaction medium.

4. Efficiency of Transformation: The efficiency of the transformation of inbred yellow Iochief corn using *A. tumefaciens* strain C58 was also investigated. The results are shown in FIG. 3C where all ten lanes contain the product produced by incubating cell-free extracts from single C58-inoculated seedlings with nopaline dehydrogenase reaction medium for six hours. As can be seen, 9 out of 10 seedlings were transformed. Additional single seedling assays were done using seedlings transformed with either B6 or C58. Of the 150 total single seedling assays done with either strain B6 or C58, sixty percent were transformed.

5. Controls: To rule out the possibility that the nopaline produced was a consequence of some secondary and uninteresting event, several additional controls were done. As shown in FIG. 4A, electrophoresis of cell-free sonicates of a suspension of C58 cultured for 48 hours, as described above in Example II, part A, failed to disclose any stored nopaline, lanes 3 and 4. Furthermore, when these sonicates were mixed with nopaline dehydrogenase reaction medium and incubated for four hours at 25° C., no nopaline dehydrogenase activity could be detected. See FIG. 4B, lanes 6 and 7 where the products of this incubation were electrophoresed. Thus, nopaline dehydrogenase activity was not found in bacterial cultures 48 hours old. Also, nopaline dehydrogenase reaction medium alone did not contain any nopaline. See FIG. 4B, lane 5, where this reaction medium alone was electrophoresed. Similarly, no evidence is found of this dehydrogenase in uninfected corn seedlings. See FIG. 4C which shows an electrophoretogram in which lanes 6-10 contain the product produced by incubating cell-free extracts of uninfected single seedlings for four hours with nopaline dehydrogenase reaction medium. These results confirm that the presence of nopaline dehydrogenase activity in the cell-free extracts of C58-inoculated seedlings is due to the transformation of the seedlings and not to some secondary and uninteresting event.

EXAMPLE III

A. Transformation of Corn

Strain C58 was cultured as described above in Example II, part A, and inbred yellow Iochief corn was sterilized, germinated, inoculated and incubated as described above in Example II, part B. After 7 days of incubation, the infected seedlings were planted in pots containing potting soil.

B. Assays

1. Assay For Enzymatic Activity in Leaves of Embryonic Origin: Three weeks after planting, three leaves of embryonic origin from three separate plants were assayed for the presence of nopaline dehydrogenase activity. The leaves chosen for the assay were the first leaves from the base of the plant which had not enlarged. The embryonic leaves are derived from differentiated structures present in the seedlings at the time of inoculation, but these differentiated structures are not located in the inoculated area.

Figure 5A:
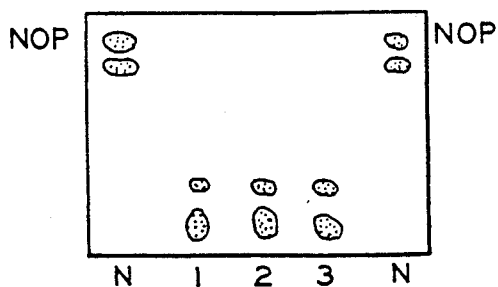
FIG. 5A is a drawing of a developed electrophoretogram which is the result of the electrophoresis of the products produced by incubating the cell-free extracts of single embryonic leaves from plants grown from C58-inoculated yellow Iochief corn seedlings with nopaline dehydrogenase reaction medium.

To perform the assay, the three embryonic leaves were individually homogenized in Tris-HCl buffer, centrifuged and assayed for enzymatic activity as described above in Example II, part C, for the seedlings. The results of the electrophoresis of the product produced by incubating the cell-free extracts of the three embryonic leaves with nopaline dehydrogenase reaction medium for twelve hours are shown in FIG. 5A where lanes 1, 2 and 3 contain the products of this incubation. As can be seen from FIG. 5A, none of the cell-free extracts of the embryonic leaves contained nopaline dehydrogenase activity demonstrating that these leaves had not been transformed by the inoculation procedure.

2. Assay For Enzymatic Activity in Leaves of Meristematic Origin: Leaves derived from the meristem (all leaves besides embryonic leaves) were assayed for the presence of nopaline dehydrogenase 7 weeks after the planting of the seedlings. The meristem is tissue composed of small, rapidly dividing, undifferentiated cells which are capable of dividing to produce organs and other differentiated tissue. Meristematic tissue which differentiates into leaves is located in the inoculated area.

To perform the assay, sections were dissected out of the meristem-derived leaves, and the dissected sections from each leaf were homogenized together in Tris-HCl buffer, centrifuged and assayed for enzymatic activity as described above in Example II, part C, for seedlings. The sections of the leaves which were used for the assay are indicated by the numerals 2 and 3 in FIG. 5B. The section designated by the numeral 3 was dissected by cutting along lines 6 and 7. Line 7 is coincident with the midrib 4 of the leaf. Section 3 is located at the base of the leaf which is normally attached to the plant. The base of the leaf is the growing end of the leaf, and this area contains the newest cells on the leaf. The sections designated by the numeral 2 were dissected by cutting along line 5 which is perpendicular to the midrib 4. Sections 2, 2 are at the tip of the leaf, and they contain the oldest cells on the leaf. Each section 2 or 3 constitutes about 1/6 of the leaf's surface area.

Figure 5C:
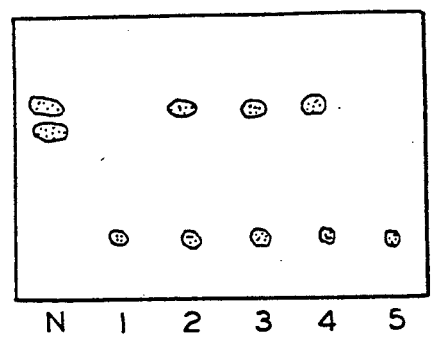
FIG. 5C is a drawing of a developed electrophoretogram showing the results of the electrophoresis of the products produced by incubating the cell-free extracts of the dissected sections of four meristematic leaves from four separate plants grown from C58-inoculated yellow Iochief corn seedlings with nopaline dehydrogenase reaction medium.

The results of the electrophoresis of the product produced by incubating the cell-free extracts of these sections of four leaves of meristematic origin taken from four separate plants with nopaline dehydrogenase reaction medium are shown in FIG. 5C. In FIG. 5C, lane 1 contains nopaline dehydrogenase reaction medium, and lanes 2-5 contain the products produced by incubating the cell-free extracts of the leaves with nopaline dehydrogenase medium for twelve hours. As shown there, cell-free extracts of 3 out of 4 leaves produced nopaline demonstrating that they contained nopaline dehydrogenase activity. Since these leaves are derived from meristematic tissue by cell division and differentiation, these results demonstrate that the cells in the inoculated area of the seedling were able to pass on the ability to synthesize nopaline dehydrogenase to future generations of corn cells. Thus, these results demonstrate that transformation of cells in the area inoculated and of cells derived from these cells has taken place.

Figure 5D:
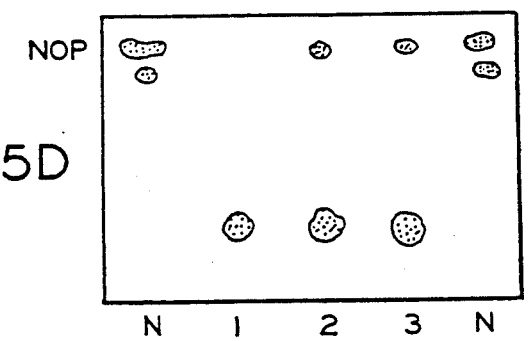
FIG. 5D is a drawing of a developed electrophoretogram showing the results of the electrophoresis of the products produced by incubating cell-free extracts of pollen from individual plants grown from C58-inoculated yellow Iochief corn seedlings with nopaline dehydrogenase reaction medium.
Figure 5B:
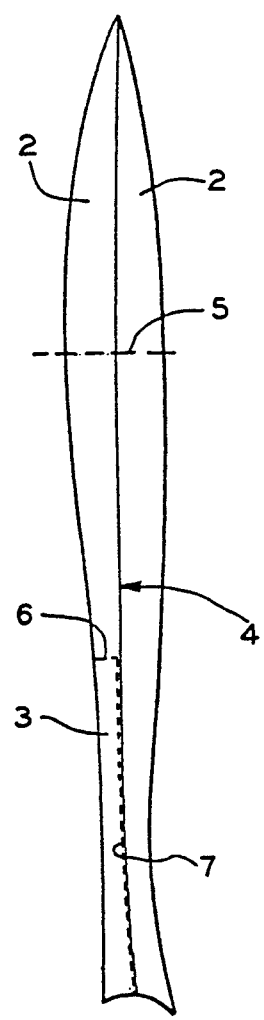
FIG. 5B is a drawing of a corn leaf of meristematic origin showing the areas dissected for assay for nopaline dehydrogenase activity.

3. Assay For Enzymatic Activity in Pollen: Sixty days after the planting of the seedlings, samples of the pollen of two plants were individually assayed for the presence of nopaline dehydrogenase. To perform the assay, 0.5 to 1.0 milliliter of pollen containing approximately $5-10 \times 10^5$ grains of pollen was homogenized in Tris-HCl buffer, centrifuged and assayed for enzymatic activity as described above in Example II, part C, for seedlings. The results of the electrophoresis of the products produced by incubating the cell-free extracts of the pollen from the two plants with nopaline dehydrogenase reaction medium for twelve hours are shown in FIG. 5D where lanes 2 and 3 contain the products of this incubation, and lane 1 contains nopaline dehydrogenase reaction medium. As can be seen from that figure, pollen from both of the plants contained nopaline dehydrogenase activity. Since the pollen is derived from the apical meristem by cell division and differentiation, these results, like the results for the leaves of meristematic origin above, demonstrate that transformation has taken place.

4. Assay for Enzymatic Activity in Seedlings Derived from Transformed Pollen: Pollen from the two transformed plants identified above in part B3 is used to fertilize ears on plants grown from uninfected yellow Iochief corn seed. The $F_1$ seeds produced by the fertilized plants as a result of this mating are harvested and are germinated and incubated as described above in Example I, parts B and C, except that the seedlings are not inoculated. After 7-14 days of incubation, the seedlings are assayed for enzymatic activity as described above in Example II, part C. Cell-free extracts of the seedlings are found to produce nopaline showing that this $F_1$ generation of seedlings is transformed.

5. Assay for Enzymatic Activity in Leaves of Embryonic Origin Taken from Plants Derived From Transformed Pollen: Seeds produced by the mating described above in part B4 of this example are harvested and are germinated and incubated as described above in Example I, parts B and C, except that the seedlings are not inoculated. After 7-14 days incubation, the seedlings are planted as described above in part A of this example. Three weeks after planting, embryonic leaves are assayed for nopaline dehydrogenase activity as described above in part B1 of this example, and cell-free extracts of the embryonic leaves produce nopaline showing they are transformed.

EXAMPLE IV

A. Transformation of Corn

Yellow Iochief corn was sterilized, germinated, inoculated and further incubated for 7-14 days as described above in Example I, Parts B and C, except that separate groups of corn seedlings were inoculated with either *A. tumefaciens* strain A348, strain JK 195 or strain 238MX.

The A348 strain carries the broad host range plasmid pTiA6NC from strain A6NC. It is vir+, and it codes for the production of lysopine dehydrogenase in suitable plant hosts. Strain A6NC and plasmid pTiA6NC are described by Sciaky et al. in *Plasmid,* 1, 238 (1977). The A348 used was obtained from Eugene Nester, University of Washington, Department of Microbiology and Immunology, Seattle, Wash. It was cultured as described above in Example I, part A, for strain B6.

Strains JK 195 and 238MX each carry a mutation in the critical vir region and are vir−. They cannot, therefore, convey the necessary portion of the Ti plasmid to their respective hosts. Consequently, plant extracts made from material inoculated with these bacteria would not be expected to produce any opine when added to the appropriate reaction medium.

The 238MX is similar in background and source to the A348 strain, but has the bacterial transposon Tn3 inserted in the vir region rendering it vir−. Strain 238MX was obtained from Eugene Nester (address given above). It was incubated as described in Example I, part A, for strain B6, and it was selected on YEB containing 100 ug/milliliter of carbenicilin.

The JK 195 strain is a vir− mutant derived from C58. It has the bacterial transposon Tn5 inserted in complementation group VI of the vir region. A detailed description of strain JK 195 may be found in Kao et al., *Mol. Gen. Genet.* 188, 425 (1982) and Lundguist et al., *Mol. Gen. Genet.,* 193, 1 (1984). The JK 195 used was obtained from Clarence Kado (address given above). It was also incubated as described in Example I, part A, and it was selected on YEB containing 50 ug/milliliter rifampicin.

B. Assays

Figure 3D:
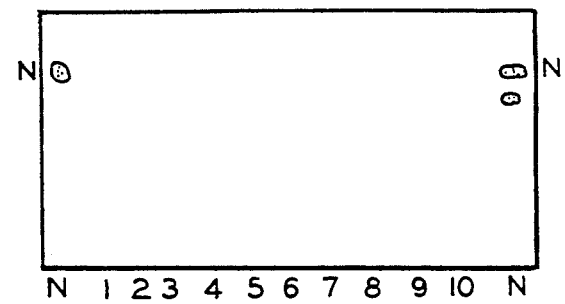
FIG. 3D is a drawing of a developed paper electrophoretogram showing the results of the electrophoresis of the products produced by incubating cell-free extracts of single yellow Iochief corn seedlings inoculated with *A. tumefaciens* strain JK 195 with nopaline dehydrogenase reaction medium.

1. Assay For Enzyme Activity in Seedlings: As is shown in FIGS. 3B and 3D, cell-free extracts of seedlings inoculated with the 238MX strain or the JK 195 strain do not produce opines. In FIG. 3B, lanes 6-10 contain the product produced by incubating the cell-free extracts of 238MX-inoculated single seedlings with the lysopine dehydrogenase reaction medium for four hours. As can be seen, none of the seedlings was transformed since no octopine was synthesized by the cell-free extracts. In FIG. 3D, all ten lanes contain the product produced by incubating the cell-free extracts of JK 195-inoculated single seedlings with nopaline dehydrogenase reaction medium for six hours. Again, none of the seedlings was transformed since no nopaline was produced.

However, the A348 strain is competent with respect to transformation. In FIG. 3B, lanes 1-5 contain the product produced by incubating the cell-free extracts of A348-inoculated single seedlings with lysopine dehydrogenase reaction medium for four hours. As can be seen, lysopine dehydrogenase was found in the cell-free extract of one out of five single seedlings inoculated with A348 showing that the seedling was transformed.

Thus, only those vir+ *A. tumefaciens* strains capable of transferring T-DNA transform corn seedlings. Those which carry mutations in the vir region and which are, therefore, transfer minus do not provoke opine synthase activity in extracts made from infected plants.

EXAMPLE V

A single colony of the *A. tumefaciens* strain T37 was inoculated into YEB, and the bacteria were incubated as described above in Example I, Part A, for strain B6.

The T37 strain is a standard wild type strain of *A. tumefaciens*. It is vir+, and it codes for the production of nopaline dehydrogenase in suitable plant hosts. It was originally obtained from John Kemp, University of Wisconsin, Department of Plant Pathology, Madison, Wis., and can currently be obtained from Anne C. F. Graves, University of Toledo, Dept. of Biology, Toledo, Ohio. It has been described in Turgeon et al, *PNAS*, 73, 3562 (1976) and in Sciaky et al, *Plasmid*, 1, 238 (1978).

Seeds of the inbred yellow Iochief strain of corn were sterilized, germinated, inoculated and further incubated for 7-14 days as described above in Example I, parts B and C, except that the corn seedlings were inoculated with strain T37 rather than strain B6.

At the end of the 7-14 day incubation period, the seedlings were assayed for enzyme activity as described above in Example II, part C. Using this procedure, nopaline production by the cell-free extracts of T37-inoculated corn seedlings was demonstrated showing that the seedlings were transformed.

EXAMPLE VI

A single colony of the *A. tumefaciens* strain C58 was inoculated into YEB, and the bacteria were incubated as described above in Example II, part A. Seeds of the inbred PA91 strain of corn were sterilized, germinated, inoculated and further incubated for 7-14 days as described above in Example I, parts B and C, for the inbred yellow Iochief strain. The PA91 strain is a standard inbred strain of corn which is commercially available. It was obtained from Jean Roberts, Eli Lilly and Co., Greenville, Ind.

Figure 6:
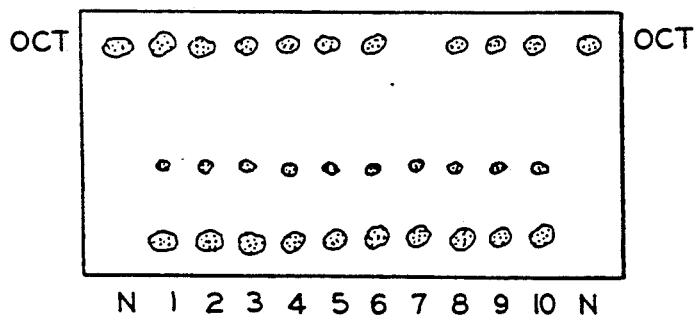
Figure 7:
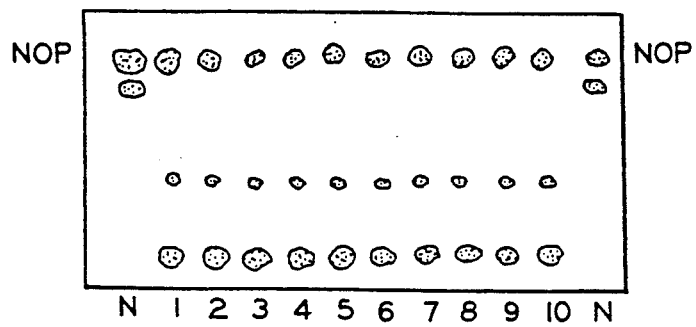

At the end of the 7-14 day incubation period, the seedlings were assayed as described above in Example II, part D. As shown in FIG. 7, nopaline production by the cell-free extracts was demonstrated showing that the PA91 strain of corn had been transformed. In FIG. 6, lanes 1-10 contain the product produced by incubating the cell-free extracts of single C-58-inoculated seedlings with nopaline dehydrogenase reaction medium for six hours. As can be seen, all ten of the cell-free extracts produced nopaline showing that the seedlings were transformed.

EXAMPLE VII

A single colony of the *A. tumefaciens* strain B6 was inoculated into a yeast extract broth, and the bacteria were incubated as described above in Example I, part A. Seeds of the inbred yellow Iochief strain of corn were sterilized, germinated, inoculated and further incubated for 7-14 days as described above in Example I, parts B and C, except that the seeds were germinated as follows. After being sterilized, the seeds were soaked for about 12 hours in sterile distilled water. They were then incubated on sterile moistened Whatman No. 3 paper in sterile Petri dishes as described above, but they were only incubated for 1.5 to 2.0 days since soaked seeds germinate in a shorter time than do unsoaked seeds.

At the end of the 7-14 day incubation period, the seedlings were assayed for enzyme activity as described above in Example I, part D. Using this procedure, octopine production by cell-free extracts of the infected seedlings was demonstrated showing that the seedlings were transformed.

EXAMPLE VIII

A single colony of the *A. tumefaciens* strain LBA 4013 was inoculated into YEB, and the bacteria were incubated as described above in Example I, part A, for strain B6. The LBA 4013 strain is a mutant strain derived from *A. tumefaciens* strain Ach5. LBA 4013 contains the wild type Ti plasmid pTiAch5 which is vir+, and LBA 4013 codes for the production of lysopine dehydrogenase in suitable plant hosts. LBA 4013 was obtained from Clegg Waldron, Eli Lilly and Co., Indianapolis, Ind. It has been described by Marton et al., in *Nature*, 277, 129 (1979).

Seeds of the inbred yellow Iochief strain of corn were sterilized, germinated, inoculated and further incubated for 7-14 days as described above in Example I, parts B and C, except that the corn seedlings were inoculated with strain LBA 4013 rather than strain B6.

At the end of the 7-14 day incubation period, the seedlings were assayed for enzyme activity as described above in Example I, part D. Using this procedure, octopine production by cell-free extracts of LBA 4013-transformed seedlings was demonstrated showing that the seedlings were transformed.

EXAMPLE IX

A. Preparation of Bacteria

A single colony of the *A. tumefaciens* strain CA19 was inoculated into YEB, and the bacteria were incubated as described above in Example I, Part A, for strain B6. The CA19 strain is derived from strain LBA 4013 and contains the pTiAch5 plasmid of LBA 4013 which is vir+ as described above in Example VIII, and strain CA19 codes for the production of lysopine dehydrogenase in suitable plant hosts.

Strain CA19 also contains the micro-Ti plasmid pCEL44. Micro-plasmid pCEL44 comprises a construct consisting of the gene coding for hygromycin phosphotransferase (aphIV) inserted between the 5' promoter and associated amino terminal region-encoding sequence of an octopine synthase gene and the 3' terminator sequence of a nopaline synthase gene. This construct is assembled between T-DNA border fragments in broad-host-range vector pKT210. Micro-plasmid pCEL 44 is capable of transforming plant cells and rendering them resistant to hygromycin.

Strain CA19 is prepared as follows.

Figure 8:
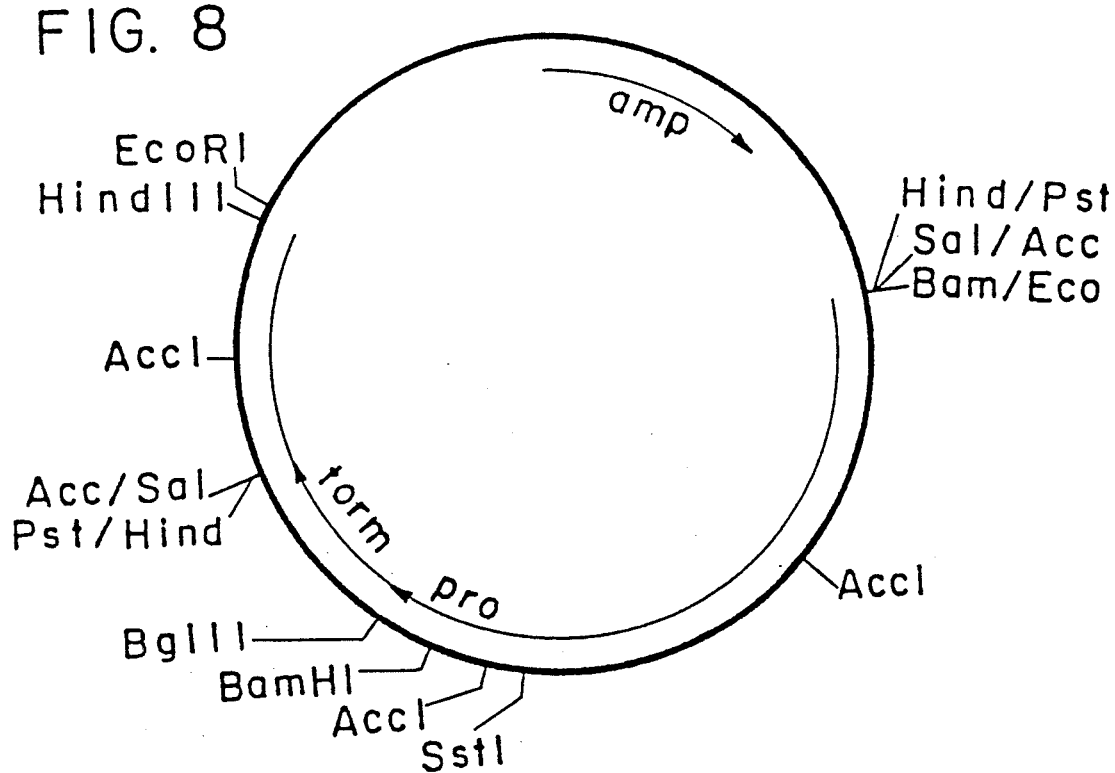

1. Culture of *Escherichia coli* RR1ΔM15/pCEL30 and Isolation of Plasmid pCEL30: Plasmid pCEL30 comprises the right-hand border sequence of the T-DNA and 5' end of the octopine synthase (ocs) gene derived from plasmid pTiA66. A linker containing a unique BglII site is fused in the 11th codon of the ocs gene. Attached to the linker are the termination and polyadenylation signals of the nopaline synthase gene of plasmid pTiC58. Attached to these sequences is a sequence which includes the left-hand border sequence of the T-DNA derived from plasmid pTiA66. A restriction site and function map of plasmid pCEL30 is given in FIG. 8.

Plasmid pCEL30 can be conventionally isolated from *Escherichia coli* K12 RR1ΔM15/pCEL30. *E. coli* RR1ΔM15/pCEL30 is on deposit at the Northern Regional Research Laboratory (NRRL), Peoria, Ill. 61604, and has accession number NRRL B-15915.

The isolation is performed as follows. *E. coli* RR1ΔM15/pCEL30 is grown in 750 ml of L medium (10 g/l caesin hydrolysate, 5 g/l yeast extract, 5 g/l NaCl, 1 g/l glucose, pH 7.4) containing ampicillin at 50 mg/ml according to conventional microbiological procedures. The culture is harvested after 24 hours incubation at 37° C. with vigorous shaking.

The culture is centrifuged, and the cell pellet is resuspended in 50 ml freshly-prepared lysis buffer (50 mM Tris-HCl, pH 8, 10 mM EDTA, 9 mg/ml glucose, 2 mg/ml lysozyme). After 45 minutes incubation on ice, the suspension is mixed with 100 ml of a solution that is 0.2N NaOH and 1% SDS. The suspension is then kept on ice for a further 5 minutes. Another 90 ml of 3M sodium acetate is added, and the mixture is maintained on ice for an additional 60 minutes.

Cell debris is removed by centrifugation, and the supernatant is mixed with 500 ml ethanol. After 2 hours at −20° C., nucleic acid is pelleted by centrifugation and is resuspended in 90 ml of 10 mM Tris-HCl, pH 8, 10 mM EDTA.

The nucleic acid solution is mixed with 90 gm cesium chloride, and 0.9 ml of a solution containing 10 mg/ml of ethidium bromide. This mixture is then centrifuged at 40,000 rpm for 24 hours to purify the plasmid DNA. The plasmid DNA band is recovered and is then recentrifuged at 40,000 rpm for 16 hours. The plasmid DNA band is again recovered and freed of cesium chloride and ethidium bromide by conventional procedures. It is next precipitated with 2 volumes of ethanol containing 90 g/l ammonium acetate. The pelleted DNA is dissolved in TE buffer (10 mM Tris-HCl, pH 8, 1 mM EDTA) at a concentration of 0.2 mg/ml.

2. Culture of *E. coli* JA221/pOW20 and Isolation of Plasmid pOW20: *E. coli* JA221/pOW20 is grown as described for *E. coli* RR1ΔM15/pCEL30 in part A1 of this example, and plasmid pOW20 is prepared as described for plasmid pCEL30 in part A1of this example.

3. Construction of E. coli RR1ΔM15/pCEL40: Five μg of plasmid pCEL30 DNA are digested with 50 units of BglII restriction enzyme in a 150 μl reaction mixture of the composition recommended by the enzyme manufacturer. Restriction and other enzymes can be readily obtained from the following sources:

Bethesda Research Laboratories, Inc. Box 6010 Rockville, Md. 20850

Boehringer Mannheim Biochemicals 7941 Castleway Drive P.O. Box 50816 Indianapolis, Ind. 46250

New England Bio Labs., Inc. 32 Tozer Road Beverly, Mass. 01915

Digestion is allowed to proceed for 90 minutes at 37° C.

The reaction mixture is first mixed with 8.75 μl of 0.5M Tris-HCl, pH 8, 1 mM EDTA and then with 1.25 units of calf intestinal phosphatase (which can be purchased from Boehringer Mannheim) and incubated at 37° C. for 15 minutes. The mixture is next extracted with buffered phenol, then with ether and is precipitated with 2 volumes of ethanol containing ammonium acetate. After 30 minutes at −70° C., the DNA is pelleted and redissolved in TE buffer at a concentration of 10 μg/ml.

About 20 μg of plasmid pOW20 DNA is digested with the restriction enzymes BamHI and BglIII according to the enzyme manufacturer's recommended procedures to obtain the aphIV gene. The aphIV gene is an *E. coli* gene which makes plants containing the gene resistant to hygromycin.

The DNA fragments resulting from this digestion are fractionated by conventional methods of agarose gel electrophoresis and isolated by entrapment on a piece of NA-45 DEAE paper (Schleicher & Schuell Inc., Keene, N.H. 03431) inserted into the gel during electrophoresis. DNA is eluted from the paper by spinning the paper for 5 seconds with a sufficient amount of a high salt buffer (1.0M NaCl; 0.1 mM EDTA; and 20 mM Tris, pH 8.0) to cover the paper in a microcentrifuge. The paper is incubated at 55–60° C. for 10–45 minutes with occasional swirling. The buffer is removed, and the paper washed with about 50 μl of buffer. The DNA is extracted first with phenol and then with ether and is resuspended in TE buffer at a concentration of about 25 μg/ml.

Ten ng of the phosphatased, BglII-cut plasmid pCEL30 is mixed with 50 ng of the purified ~1.3 kb BamHI-BglII fragment of plasmid pOW20 in a 15 μl ligase buffer (50 mM Tris-HCl, pH 7.6; 10 mM MgCl$_2$; 10 mM DTT; and 1 mM ATP) containing 0.8 units of T4 DNA ligase (BRL). The mixture is incubated overnight at 15° C.

The ligation mixture is mixed with 15 μl sterile 60 mM CaCl$_2$ solution. Next, 70 μl of a suspension of competent *E. coli* RR1ΔM15 cells, which has been stored 20× concentrated in 30 mM CaCl$_2$, 15% glycerol at −70° C., are added. After 60 minutes on ice, the transformation mixture is heat-treated at 42° C. for 2 minutes and is then incubated with 0.5 ml L medium for 90 minutes at 37° C.

Samples of the mixture are spread on L medium containing ampicillin at 50 mg/l and solidified with agar at 15 g/l. These samples are then incubated overnight at 37° C. to permit growth of colonies from transformed cells.

Colonies resulting from the transformation are inoculated into 5 ml L medium containing ampicillin at 50 mg/ml and grown overnight at 37° C. Plasmid DNA is prepared from 1 ml samples of these cultures by the procedure of Holmes & Quigley, *Analytical Biochemistry*, 114, 193 (1981) and is redissolved in 50 μl of TE buffer.

4. Construction of Micro-Ti Plasmid pCEL44: Since plasmid pCEL40 is not capable of replication in Agrobacterium, the micro T-DNA of plasmid pCEL40 was first transferred, as an EcoRI fragment, into broad-host-range vector pKT210. This broad-host-range vector is available from Plasmid Reference Center, Stanford University, Palo Alto, Calif. 94305.

Five μg of plasmid pKT210 are digested with 50 units of EcoRI restriction enzyme in a 150 μl reaction of a composition recommended by the enzyme manufacturer. After 90 minutes at 37° C., the reaction is treated with calf intestinal phosphatase as described above in part A3 of this example and is dissolved in TE buffer at a concentration of 10 μg/ml.

Fifteen μl of a preparation of plasmid pCEL40 DNA, grown as described above in part A3 of this example, are digested with 10 units of EcoRI restriction enzyme in a 20 μl reaction at 37° C. for 90 minutes and are then extracted with phenol, followed by extraction with ether. The digested DNA is precipitated with 2 volumes of ethanol containing ammonium acetate at −20° C. and is redissolved in 20 μl TE buffer.

Ten ng of phosphatased, EcoRI-cut pKT210 are ligated with 5 μl of EcoRI-cut pCEL40 as described above in part A3 of this example, and transformed into *E. coli* RR1ΔM15 as described above in part A3 of this example.

Figure 9:
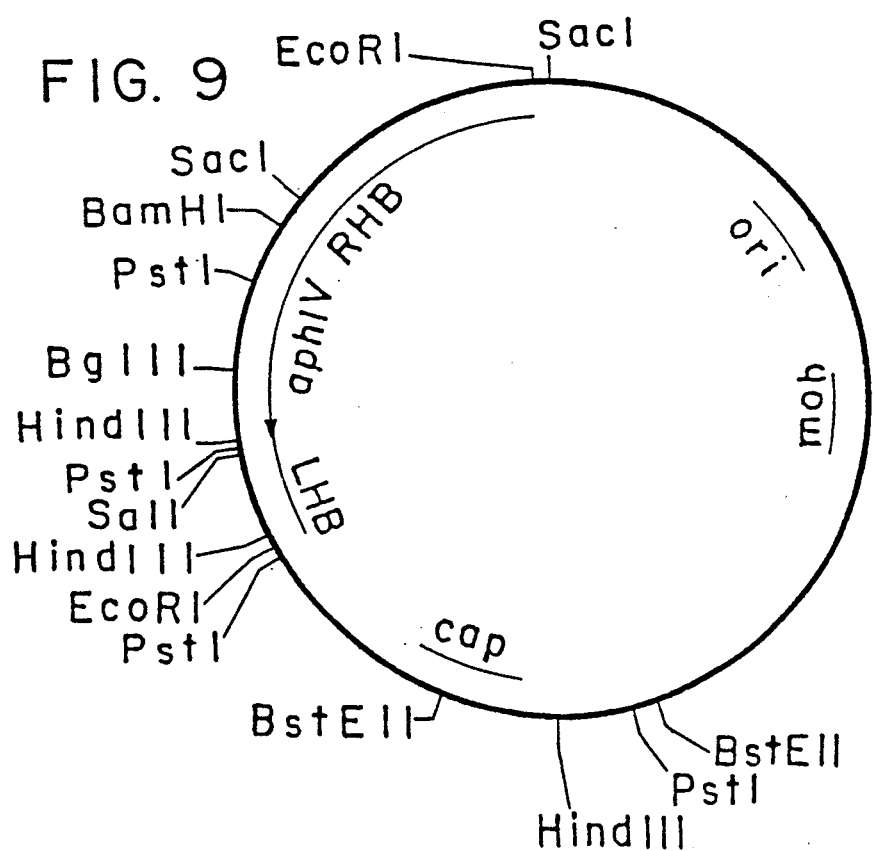

Transformed cells containing pCEL44 are selected by their ability to grow on solidified L medium containing chloramphenicol at 10 mg/l. A restriction site and function map of pCEL44 is provided in FIG. 9.

5. Conjugation of pCEL44 Into *A. tumefaciens* LBA4013 to form Strain CA19: *E. coli* K12 RR1ΔM15/pCEL44 and *E. coli* pRK2013 are grown overnight at 37° C. on solidified L medium. *A. tumefaciens* LBA4013 is grown for 2 days at 28° C. on solidified L medium.

One loop of *E. coli* K12 RR1ΔM15/pCEL44, one loop of *E. coli* pRK2013 and one loop of *A. tumefaciens* LBA 4013 are mixed in 1 ml of 30 mM magnesium sulfate solution. Next, a drop of the mixture is placed on solidified TY medium (5 g/l caesin hydrolysate, 5 g/l yeast extract, 15 g/l agar) and incubated at 28° C. overnight.

The bacterial growth is resuspended in 3 ml of 10 mM magnesium sulfate solution and 0.1 ml samples of serial dilutions are spread on solidified TY medium containing 100 mg/l nalidixic acid and 2 mg/l chloramphenicol and incubated at 28° C.

Transconjugants give rise to individual colonies after 2 to 4 days growth. These are inoculated singly into 25 ml liquid TY medium containing 100 mg/l nalidixic acid and 2 mg/l chloramphenicol and incubated at 28° C. with shaking for another 2 days. The plasmid content of the transconjugants is then checked by the method of Casse et al. (*Journal of General Microbiology* 113:229-242; 1979), and strain CA19 containing the wild type pTiAch5 plasmid and the pCEL44 plasmid is isolated.

The CA19 used to practice the method of the present invention was obtained from Clegg Waldron, Eli Lilly and Co., Indianapolis, Ind. The preparation of strain CA19 has also been described in Waldron et al., *Plant Molec. Biol.*, 5, 103 (1985) which is incorporated herein by reference.

B. Transformation of Corn

Seeds of the inbred yellow Iochief strain of corn were sterilized, germinated, inoculated and further incubated for 7-14 days as described above in Example I, parts B and C, except that the corn seedlings were inoculated with strain CA19 rather than strain B6.

C. Assays

1. Assay of Seedlings for Lysopine Dehydrogenase Activity: At the end of the 7-14 day incubation period, the seedlings were assayed for enzyme activity as described above in Example I, part D. The results are shown in FIG. 6 where lanes 1-10 contain the product produced by incubating cell-free extracts of single CA19-inoculated seedlings with lysopine dehydrogenase for four hours. As can be seen there, octopine production in 9 out of 10 cell-free extracts of single CA19-inoculated corn seedlings was demonstrated showing that the seedlings contained lysopine dehydrogenase and were transformed.

2. Assay of Seedlings for Hygromycin Resistance: Some seedlings which were inoculated with strain CA19 were incubated only for 3-4 days after inoculation, at which time they were assayed for resistance to hygromycin as follows. The seedlings were dissected away from the endosperm and scutellum (see FIGS. 1A and 1B) and cut into approximately 3 mm cross sections. The cross sections were cultured for three weeks on Duncan's medium (described by Duncan et al. in *Planta*, 165, 322 (1985)) supplemented with 200 ug/ml each carbenicillin (Sigma) and vancomycin (Lilly) or on BN4 medium (Murashige and Skoog major and minor salts (described in *Physiol. Plant*, 15 473 (1962)), 4 mg/l 2,4-dichlorophenoxy acetic acid as auxin, 9 g/l Difco Bactoagar and 20 g/l sucrose) supplemented with 200 μg/ml each carbenicillin and vancomycin, in the dark, at 25° to 27° C., followed by another three-week passage on those antibiotics.

To test the response to hygromycin of the tissue cultures derived from the corn seedlings, either whole cross sections plus the tissue which has grown up from the cross sections or 100 mg callus samples are placed onto about 50 ml of Duncan's medium or of BN4 medium supplemented with the aforementioned concentrations of vancomycin and carbenicillin and containing about 125 μg/ml of hygromycin B (Lilly) contained in Falcon 1005 Petri dishes. This test is read after three weeks of incubation in the dark at 27° C., by visually checking for growth. Cultures that are growing are light in color and show an increase in size. Using this test, positive growth phenotypes are recovered from cultures derived from CA19-inoculated seedlings showing that the seedlings are transformed by the heterologous hygromycin gene.

EXAMPLE X

A. Preparation of an *A. tumefaciens* Strain Carrying the Gene Conferring Resistant to the Herbicide Glyphosate 1. Culture of *E. coli* RR1ΔM15/pCEL30 and Isolation of Plasmid pCEL30: *E. coli* RR1ΔM15/pCEL30 is grown as described above in Example IX, part A1, and plasmid pCEL30 is isolated as described in Example IX, part A1.

2. BqlII Digestion of Plasmid pCEL30 and Treatment With Calf Intestinal Phosphatase: Five μg of plasmid pCEL30 DNA are digested and treated with calf intestinal phosphatase as described above in Example IX, part A3.

3. Isolation of Glysophate-Resistant EPSP Sunthase Gene: A gene coding for a glyphosate-resistant 5-enolphyruvylshikimate 3-phosphate synthase gene (GREPSPS gene) is isolated as described by Comai et al. in *Nature*, 317, 714 (1985) and by Stalker et al., *J. Biol. Chem.*, 260, 4724 (1985) which are incorporated herein by reference. In the final steps of this procedure, the GREPSPS gene, in a BamHI fragment cut from plasmid pPMG34, is cloned into plasmid pUC7 to give plasmid pPMG38. The GREPSPS gene is then excised from plasmid pPMG38 as an EcoRI fragment. The EcoRI fragment is then modified using a suitable commercially available molecular linker so that it is able to ligate with the unique BglII site on the BqlII-digested pCEL30 plasmid and so that the EcoRI site is removed.

The herbicide glyphosate (N-phosphonomethylglycine) is a widely used broad-spectrum herbicide that kills both weed and crop species. It inhibits a metabolic step in the biosynthesis of aromatic compounds, and the cellular target of glyphosate is 5-enolphyruvyl shikimate 3-phosphate synthase (EPSP synthase) which catalyzes the formation of 5-enolpyruvylshikimate 3-phosphate from phosphoenolpyuvate and shikimate, and inhibition of this step of the shikimate pathway eventually leads to cellular death. The GREPSPS gene is a mutant allele of the aroA locus of *Salmonella typhimurium* which encodes a EPSP synthase in which the substitution of a serine for proline causes a decreased affinity of the enzyme for glyphosate.

4. Ligation: Ten ng of the phosphatased, BglII-cut plasmid pCEL30, as prepared above in Example IX, part A3, are mixed with 50 ng of the GREPSPS gene (including the attached linker) in a 15 μl ligase buffer containing 0.8 units of T4 DNA ligase. The mixture is incubated overnight at 15° C. The ligation mixture is used to transform competent *E. coli* RR1ΔM15 cells as described in Example IX, part A3.

5. Construction of Micro-Ti Plasmid Carrying the GREPSPS Gene: After selection of transformed cells produced as described in part A4 of this example on L medium containing ampicillin as described above in Example IX, part A3, the plasmids from the transformed *E. coli* RR1ΔM15 cells are transferred as described above in Example IX, part A4, as an EcoRI fragment, into broad- host-range vector pKT210.

6. Conjugation Into *A. tumefaciens* LBA 4013: The plasmid carrying the GREPSPS gene on broad-host-range vector pKT210 is transferred into *A. tumefaciens* strain LBA 4013 by conjugation as described above in Example IX, part A5. The resulting transconjugants are selected as described above in Example IX, part A5, and a new strain of *A. tumefaciens* carrying the GREPSPS gene which is herein referred to as strain LBA 4013/GREPSPS, is isolated.

B. Transformation of Corn

Seeds of the inbred yellow Iochief strain of corn are sterilized, germinated, inoculated and further incubated as described above in Example I, parts B and C, except that the corn seedlings were inoculated with strain LBA 4013/GREPSPS rather than strain B6. After 7 days of incubation, the infected seedlings are planted in pots in potting soil.

C. Assays

1. Assay For Enzymatic Activity in Pollen: Sixty days after the planting of the seedlings, samples of the pollen of five plants are individually assayed for the presence of lysopine dehydrogenase as described above in Example III, part B. The results of the electrophoresis of the products produced by incubating the cell-free extracts of the pollen of the five plants show that three out of five of the cell-free extracts of the pollen produce octopine showing that the pollen is transformed.

2. Assay for EPSP Synthase Activity: Leaves derived from the meristem are assayed seven weeks after planting of the seedlings for EPSP synthase activity according to the method of Boocock and Coggins, *FEBS Letters*, 154, 127 (1983) which is incorporated herein by reference. Five leaves from five separate plants are assayed, and three are found to contain EPSP synthase activity showing that transformation had occurred.

3. Assay For Resistance To Glyphosate: The three plants found to contain EPSP synthase activity in their leaves as a result of the assay in part C2 of this example are sprayed with the equivalent of 0.5 kg/hectare of the isopropylamine salt of glyphosate. All three plants show considerable tolerance to glyphosate as compared to controls.

None of the foregoing description of the preferred embodiments is intended in any way to limit the scope of the invention which is set forth in the following claims. Those skilled in the art will recognize that many modifications, variations and adaptations are possible.

EXAMPLE XI

A. Transformation of Corn

Strain CA19 was cultured as described in Example IX, part A, and yellow Iochief corn was sterilized, germinated, inoculated with CA19 and inoculated as described in Example I, parts B and C. Seedlings were also inoculated with *A. tumefaciens* strain CA17 which is identical to strain CA19, except that the gene that codes for hygromycin resistance is inserted in the antisense direction. Finally, seedlings were also inoculated with YEB alone. After seven days of incubation, all of the inoculated seedlings were planted.

B. Assays

1. Assay For Enzymatic Activity in the Upper Leaves of Transformed Plants: As the plants reached sexual maturity, their upper leaves were assayed for the presence of lysopine dehydrogenase activity as described in Example III, part B2, except that lysopine dehydrogenase reaction medium was used. Leaves of five plants derived from seedlings inoculated with CA19, of two plants derived from seedlings inoculated with CA17 and of three plants inoculated with YEB were assayed.

Figure 14:
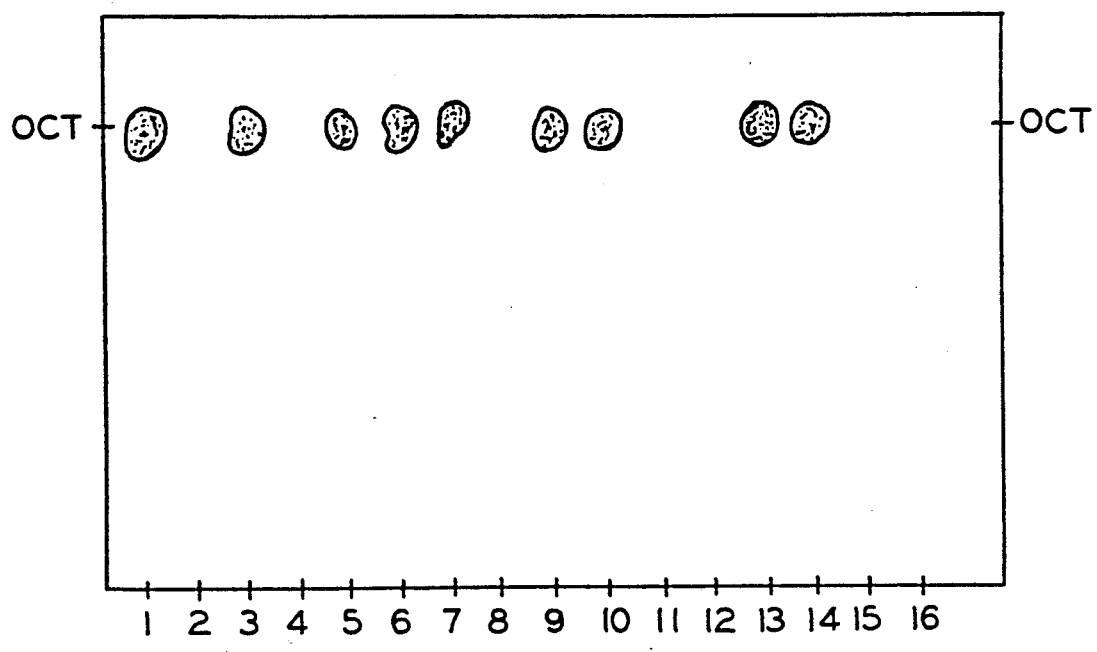

The results are shown in FIG. 14. In FIG. 14, the lanes contain the following materials:

| Lane | Plant Code No. | Proculum Used on Seedling | Plant Part Sampled | Comments |
|---|---|---|---|---|
| 1 | — | — | — | Synthetic octopine standard |
| 2 | S-1 | YEB | Flag leaf | — |
| 3 | 19-6 | CA19 | Leaf below flag leaf | — |
| 4 | 19-6 | CA19 | Tiller | — |
| 5 | 17-4 | CA17 | Ear shoot | — |
| 6 | 19-3 | CA19 | Ear shoot | — |
| 7 | 19-3 | CA19 | Leaf below flag leaf | — |
| 8 | S-5 | YEB | Leaf below flag leaf | — |
| 9 | 17-3 | CA17 | Leaf below flag leaf | — |
| 10 | 17-3 | CA17 | Second leaf below flag leaf | — |
| 11 | 19-4 | CA19 | Leaf below flag leaf | — |
| 12 | S-8 | YEB | Leaf below flag leaf | — |
| 13 | 19-5 | CA19 | Flag leaf | — |
| 14 | 19-5 | CA19 | Leaf below flag leaf | — |
| 15 | 19-2 | CA19 | Flag leaf | — |
| 16 | 19-2 | CA19 | Leaf below flag leaf | — |

As shown in FIG. 14, none of the extracts of leaves derived from YEB-inoculated seedlings produced octopine, whereas 8 out of 12 extracts of leaves derived from CA19-inoculated and CA-17-inoculated seedlings produced octopine.

2. Assay For Bacteria In Upper Leaves of Transformed Plants: Aliquots of the extracts of the leaves used in the lysopine dehydrogenase assay described in part B2 of this example were also plated to determine if any bacteria were present in these extracts. Any bacterial colonies growing up as a result of these platings were transferred to a lactose-containing medium diagnostic for Agrobacteruim. None of the bacteria that grew up as a result of the original platings (either in extracts of leaves derived from YEB-inoculated seedlings, from CA19-inoculated seedlings or CA17-inoculated seedlings) oxidized lactose to lactic acid showing that none of them were Agrobacterium of the type used to inoculate the seedlings.

3. Assay For Enzymatic Activity in Leaves of $F_1$ Plants: Using the results of the above assay, plants 19-5 and 19-3 were chosen for further study. Plant 19-5 was chosen because extracts of both of the two top leaves were positive for lysopine dehydrogenase activity indicating that this plant might have a transformed sector extending into the tassel. Plant 19-3 was chosen because extracts of its ear shoot and leaf below the flag leaf were positive for lysopine dehydrogenase activity indicating that this plant might have a transformed sector extending into the ear and a transformed sector extending into the tassel.

These two plants were self pollinated. Then, 26-27 days post pollination, the immature progeny ears of plants 19-3 and 19-5 were removed from the plants and surface sterilized. The late maturity embryos of the ears from these plants were excised and planted on half-strength Murashige and Skoog medium. The embryos were allowed to germinate sterilely in the light for 8-10 days, at which time they were planted in soil.

The meristem-derived leaves of the $F_1$ seedlings which survived transplanting to soil were assayed for lysopine dehydrogenase activity as described in Example III, part B2, except that lysopine dehydrogenase reaction medium was used. The intensity of the staining of the spots on the electrophoretogram that co-migrated with octopine was rated. The results are presented in Table 1. As shown there, some of the leaves of the seedlings produced octopine, showing the sexual transmission of this trait to the $F_1$ generation.

| Rating | Leaves From Plants Produced By Embryos Taken From Plant 19-3 | Leaves From Plants Produced By Embryos Taken From Plant 19-5 |
| --- | --- | --- |
| Dead (no test) | 85 | 9 |
| Negative | 71 | 76 |
|  | (25 subsequently died) | (7 subsequently died) |
| Weak Positive | 5 | 17 |
|  | (3 subsequently died) | (0 subsequently died) |
| Positive | 34 | 27 |
|  | (8 subsequently died) | (3 subsequently died) |
| Strong Positive | 3 | 3 |
|  | (0 subsequently died) | (0 subsequently died) |

TRANSFORMATION OF OTHER SPECIES OF GRAMINEAE

EXAMPLE XII

A single colony of the *A. tumefaciens* strain B6 was inoculated into a yeast extract broth, and the bacteria were incubated as described above in Example I, part A. Seeds of rye were sterilized, germinated, inoculated and further incubated for 7-14 days as described above in Example I, parts B and C. The seedlings were inoculated in the apical meristem, an area of rapidly dividing cells that gives rise to the germ line cells.

Figure 10:
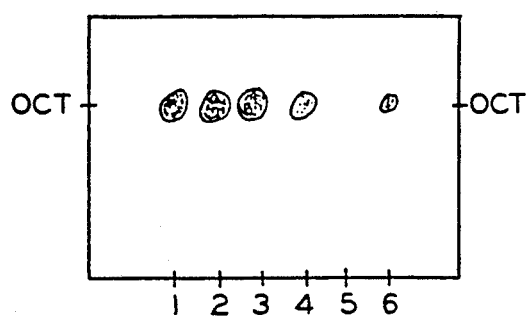

At the end of the 7-14-day incubation period, the seedlings were assayed for enzyme activity as described above in Example I, part D. The results of the electrophoresis of the products produced by adding the cell-free extracts of the B6-inoculated rye seedlings to lysopine dehydrogenase reaction medium are shown in FIG. 10. In that figure, lane 1 contains the synthetic octopine standard and lanes 2-6 contain the product produced by incubating the cell-free extract of single B6-inoculated rye seedlings with lysopine dehydrogenase reaction medium. The results shown in FIG. 10 demonstrate that octopine production is caused by the cell-free extracts of three out of four B-6-inoculated rye seedlings tested (lanes 2, 3, 4 and 6). These results show that the rye seedlings have been transformed by infection with the vir+ *A. tumefaciens* strain B6.

EXAMPLE XIII

A single colony of the *A. tumefaciens* strain B6 was inoculated into a yeast extract broth, and the bacteria were incubated as described above in Example I, part A. Barley seeds were sterilized, germinated, inoculated and further incubated for 7-14 days as described above in Example I, parts B and C. The seedlings were inoculated in the apical meristem, an area of rapidly dividing cells that gives rise to the germ line cells.

Figure 11:
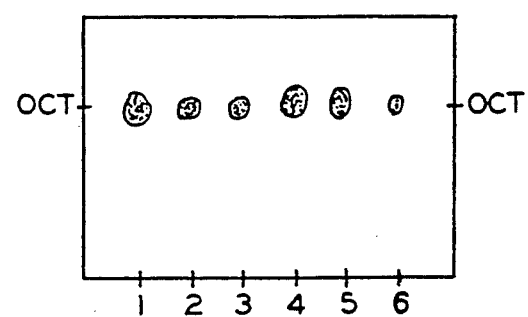

At the end of the 7-14-day incubation period, the seedlings were assayed for enzyme activity as described above in Example I, part D. The results of the electrophoresis of the products produced by adding the cell-free extracts of B6-inoculated barley seedlings to lysopine dehydrogenase reaction medium are shown in FIG. 11. In that figure, lane 1 contains the synthetic octopine standard and lanes 2-6 contain the product produced by incubating the cell-free extract of single B6-inoculated barley seedlings with lysopine dehydrogenase reaction medium. The results shown in FIG. 11 demonstrate that octopine production is caused by five out of five cell-free extracts of B6-inoculated barley seedlings tested and show that the seedlings have been transformed.

EXAMPLE XIV

A single colony of the *A. tumefaciens* strain C58 was inoculated into YEB, and the bacteria were incubated as described above in Example II, part A. Oat seeds were sterilized, germinated, inoculated and further incubated for 7-14 days as described above in Example I, parts B and C. The seedlings were inoculated in the apical meristem, an area of rapidly dividing cells that gives rise to the germ line cells.

Figure 12:
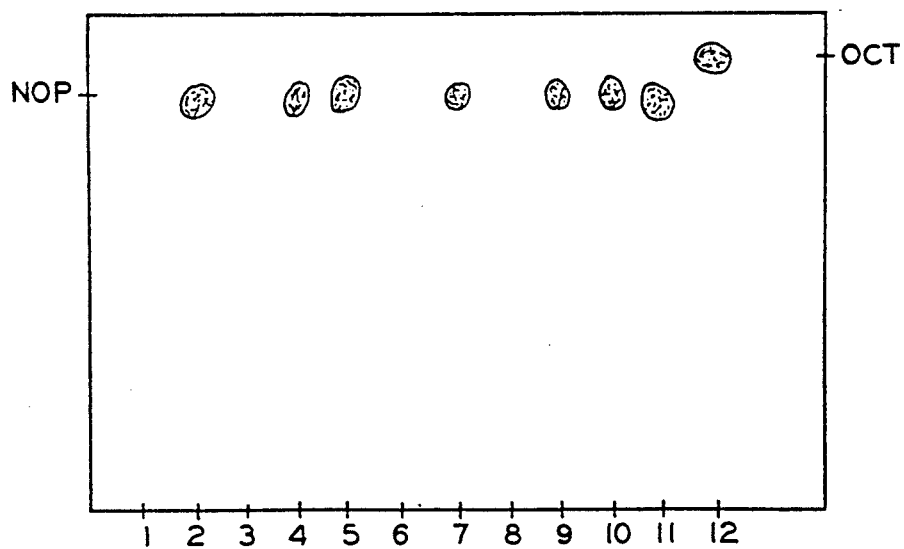

At the end of the 7-14-day incubation period, the seedlings were assayed as described above in Example II, part D. The results are shown in FIG. 12. In FIG. 12, lane 1 contains nopaline dehydrogenase reaction medium alone, lane 2 contains the nopaline standard, lanes 3-11 contain the product produced by incubating the cell-free extracts of single C58-inoculated oat seedlings with nopaline dehydrogenase reaction medium and lane 12 contains synthetic octopine. As can be seen, six out of nine of the cell-free extracts of single C53-inoculated oat seedlings produced nopaline showing that the seedlings were transformed.

EXAMPLE XV

A single colony of the *A. tumefaciens* strain C58 was inoculated into YEB, and the bacteria were incubated as described above in Example II, part A. Wheat seeds were sterilized, germinated, inoculated and further incubated for 7-14 days as described above in Example I, parts B and C. The seedlings were inoculated in the apical meristem, an area of rapidly dividing cells that gives rise to the germ line cells.

Figure 13:
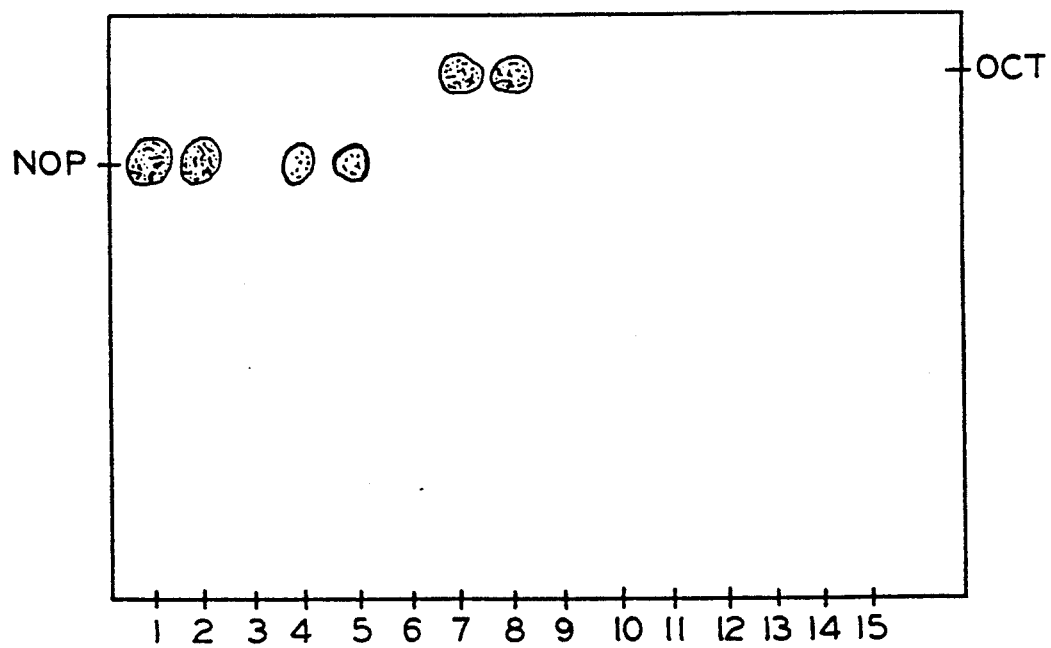

At the end of the 7-14-day incubation period, the seedlings were assayed as described above in Example II, part D. The results are shown in FIG. 13. In FIG. 13, lane 1 contains the nopaline standard, lanes 2-6 contain the product produced by incubating the cell-free extracts of single C58-inoculated wheat seedlings with nopaline dehydrogenase reaction medium, lane 7 contains synthetic octopine, lane 8 contains a mixture of synthetic octopine and lysopine dehydrogenase reaction medium and lanes 9-15 contain the product produced by incubating the cell-free extracts of single C58-inoculated wheat seedlings with lysopine dehydrogenase reaction medium. As can be seen, three out of five of the cell-free extracts of the C58-inoculated wheat seedlings produced nopaline when incubated with nopaline dehydrogenase reaction medium, showing that the seedlings were transformed. None of the cell-free extracts produced octopine when incubated with lysopine dehydrogenase reaction medium.

We claim:

1. A method of producing transformed Gramineae, said method comprising:
    making a wound in a graminaceous seedling with newly emerged radicle and stem, said wound being made in an area of the seedling containing rapidly dividing cells, wherein said area extends from the base of the scutellar node to slightly beyond the coleoptile node; and
    inoculating the wound with vir+ *Agrobacterium tumefaciens*.

2. The method of claim 1 wherein about four wounds are made in the seedling, and a total of about $10^8$ *Agrobacterium tumefaciens* cells are used to inoculate the wounds.

3. The method of claim 1 wherein the vir+ *Agrobacterium tumefaciens* contains a vector comprising genetically-engineered T-DNA.

4. The method of claim 1 or 3 wherein the Gramineae is selected from the group consisting of corn, wheat, rye, barley and oats.

* * * * *